US011630089B2

(12) United States Patent
Alhooshani et al.

(10) Patent No.: US 11,630,089 B2
(45) Date of Patent: Apr. 18, 2023

(54) YTTRIUM-CONTAINING SOL-GEL COATING, ITS USE, AND MANUFACTURE

(71) Applicant: King Fahd University of Petroleum and Minerals, Dhahran (SA)

(72) Inventors: Khalid Alhooshani, Dhahran (SA); Shehzada Muhammad Sajid Jilani, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 664 days.

(21) Appl. No.: 16/255,192

(22) Filed: Jan. 23, 2019

(65) Prior Publication Data

US 2020/0230574 A1 Jul. 23, 2020

(51) Int. Cl.
  *G01N 1/40* (2006.01)
  *G01N 30/08* (2006.01)
  (Continued)

(52) U.S. Cl.
  CPC .............. *G01N 30/08* (2013.01); *B01J 20/06* (2013.01); *B01J 20/223* (2013.01);
  (Continued)

(58) Field of Classification Search
  CPC .. G01N 30/08; G01N 1/405; G01N 2030/009; G01N 33/1826
  See application file for complete search history.

(56) References Cited

U.S. PATENT DOCUMENTS 7,622,191 B2 11/2009 Malik et al.
9,036,354 B2 4/2015 Otsuka et al.
(Continued)

FOREIGN PATENT DOCUMENTS

| CN | 105542642 A | 5/2016 |
|---|---|---|
| CN | 107091899 A | 8/2017 |
| WO | 2007/112224 A2 | 10/2007 |

OTHER PUBLICATIONS

"Sol-gel material" IUPAC. Compendium of Chemical Terminology, 2nd ed. (the "Gold Book"). Compiled by A. D. McNaught and A. Wilkinson. Blackwell Scientific Publications, Oxford (1997). Last revised: Feb. 24, 2014 https://doi.org/10.1351/goldbook.ST07586 (Year: 2014).*

(Continued)

*Primary Examiner* — Jennifer Wecker
*Assistant Examiner* — Michelle Adams
(74) *Attorney, Agent, or Firm* — Oblon, McClelland, Maier & Neustadt, L.L.P.

(57) ABSTRACT

Yttria containing hybrid organic-inorganic sol-gels may be used in coatings for capillary microextraction, optionally hyphenated to online HPLC analysis. The sol-gel reaction mixture can use an yttrium trialkoxyalkoxide, such as yttrium trimethoxyethoxide, and a [bis(hydroxyalkyl)-amino-alkyl]-terminated polydialkyl/arylsiloxane, such as [bis(hydroxyethyl)-amine] (BHEA)-terminated polydimethylsiloxane, that can undergo hydrolysis and polycondensation, to form coating materials. Capillaries coated with such sol-gels can have improved extraction efficiency compared, e.g., to pure yttria-based coatings. The CME-HPLC can analyze water samples containing analytes of varied polarity, with excellent extraction of amides, phenols, alcohols, ketones, aldehydes, and polyaromatic hydrocarbons and detection limits ranging from 0.18 to 7.35 ng/mL (S/N=3). Such capillaries can exhibit solvent stability at pH 0 to 14, RSD % between 0.6 to 6.8% (n=3), at a preparative reproducibility RSD between 4.1 and 9.9%.

20 Claims, 24 Drawing Sheets

(51) Int. Cl.
*B01J 20/06* (2006.01)
*B01J 20/22* (2006.01)
*B01J 20/28* (2006.01)
*B01J 20/32* (2006.01)
*B01J 20/34* (2006.01)
*G01N 33/18* (2006.01)
*G01N 30/00* (2006.01)

(52) U.S. Cl.
CPC ..... *B01J 20/28047* (2013.01); *B01J 20/3204* (2013.01); *B01J 20/3219* (2013.01); *B01J 20/3278* (2013.01); *B01J 20/3425* (2013.01); *B01J 20/3475* (2013.01); *G01N 1/405* (2013.01); *G01N 33/1826* (2013.01); *G01N 2030/009* (2013.01)

(56) References Cited

U.S. PATENT DOCUMENTS

2006/0131238 A1* 6/2006 Xu .................. C04B 35/553 521/154
2007/0095736 A1 5/2007 Malik et al.
2018/0001298 A1* 1/2018 Malik .................. B01J 20/226

OTHER PUBLICATIONS

"Sol-gel process" IUPAC. Compendium of Chemical Terminology, 2nd ed. (the "Gold Book"). Compiled by A. D. McNaught and A. Wilkinson. Blackwell Scientific Publications, Oxford (1997). Last revised: Feb. 24, 2014 https://doi.org/10.1351/goldbook.ST07151 (Year: 2014).*

"Siloxanes" IUPAC. Compendium of Chemical Terminology, 2nd ed. (the "Gold Book"). Compiled by A. D. McNaught and A. Wilkinson. Blackwell Scientific Publications, Oxford (1997). Last revised: Feb. 24, 2014 https://doi.org/10.1351/goldbook.S05671 (Year: 2014).*

"Silicones" IUPAC. Compendium of Chemical Terminology, 2nd ed. (the "Gold Book"). Compiled by A. D. McNaught and A. Wilkinson. Blackwell Scientific Publications, Oxford (1997). Last revised: Feb. 24, 2014 https://doi.org/10.1351/goldbook.S05670 (Year: 2014).*

Kim, T.-Y. et al. "High pH-resistant, surface-bonded sol-gel titania hybrid organic-inorganic coating for effective on-line hyphenation of capillary microextraction (in-tube solid-phase microextraction) with high-performance liquid chromatography," J. Chromatogr. A 1047 (2004) 165-174 (Year: 2004).*

Jillani, Shehzada Muhammad Sajid "Development of Sol-Gel Immobilized Sorbent for Capillary Microextraction" Dissertation, King Fahd University of Petroleum & Minerals, Dhahran, Saudi Arabia. Date Deposited: Oct. 16, 2018 (Year: 2018).*

Fang, Li. et al. "Germania-Based, Sol-Gel Hybrid Organic-Inorganic Coatings for Capillary Microextraction and Gas Chromatography," Anal. Chem. 2007, 79, 9441-9451 (Year: 2007).*

Alhooshani, Khalid R. "Sol-gel zirconia- and titania-based surface-bonded hybrid organic-inorganic coatings for sample preconcentration and analysis via capillary microextraction in hyphenation with gas chromatography," Dissertation, University of South Florida. 2005 ProQuest (Year: 2005).*

Alhooshani, K. et al. "Sol-gel approach to in situ creation of high pH-resistant surface-bonded organic-inorganic hybrid zirconia coating for capillary microextraction (in-tube SPME)," Journal of Chromatography A, 1062 (2005) 1-14 (Year: 2005).*

Segro, et al. ; Solvent-resistant sol-gel polydimethyldiphenylsiloxane coating for on-line hyphenation of capillary microextraction with highperformance liquid chromatography ; Journal of Chromatography A, vol. 1205, Issues 1-2 ; pp. 26-35 ; Sep. 26, 2008 ; Abstract Only ; 2 Pages.

Fang, et al. ; Germania-Based, Sol-Gel Hybrid Organic-Inorganic Coatings for Capillary Microextraction and Gas Chromatography ; Analytical Chemistry 79 (24) ; pp. 9441-9451 ; Nov. 10, 2007 ; Abstract Only ; 1 Page.

Alhooshani, et al. ; Sol-gel approach to in situ creation of high pH-resistant surface-bonded organic-inorganic hybrid zirconia coating for capillary microextraction (in-tube SPME) ; Journal of Chromatography A, vol. 1062, Issue 1 ; pp. 1-14 ; Jan. 7, 2005 ; Abstract Only ; 2 Pages.

* cited by examiner

YTTRIUM-CONTAINING SOL-GEL COATING, ITS USE, AND MANUFACTURE

BACKGROUND OF THE INVENTION

Field of the Invention

The present application relates to organic-inorganic hybrid sol-gels, particularly formed by condensing tris(hydroxyalkoxy) yttrium with bis(hydroxyalkyl)amine-terminated poly(di)alkylsiloxane(s), their manufacture and use, e.g., in capillary extraction and hyphenated chromatography.

Description of the Related Art

The separation of chemical substances is relevant in both preparative and analytical chemistry and related fields. Chromatography is a technique used to separate chemical substances and analytical samples. Methods have also been developed to aid chromatographic separations.

Solvent-free sample preparation techniques, such as solid-phase microextraction, have been developed by coating an outer surface of a fused silica capillary and/or fiber with a polymer. Analytes of interest can thereby be pre-concentrated on the small coated external surfaces of the fused silica capillary and/or fiber and subsequently be injected into a gas chromatograph (GC) for analysis. This procedure is commonly known as fiber solid-phase microextraction (SPME), and it has many shortcomings, including low sample capacity, difficulty in immobilizing thick coatings, thermal and/or solvent stability/robustness, technical complications for hyphenation, i.e., (serial) combination, with liquid chromatographic techniques, and susceptibility of the coated surface to mechanical damage.

In-tube solid phase microextraction or capillary microextraction (CME) was thus developed to facilitate hyphenation of the microextraction technique to liquid chromatographic techniques. Hyphenation is attractive for analyzing thermally labile compounds that are difficult or impossible to analyze using conventional gas chromatographic techniques. A disadvantage of using a fiber SPME technique is the potential for mechanical damage to the coated surface during analysis. In the case of conventional CME, mechanical damage can be avoided because the wall-coated GC capillary columns contain pre-concentrated analytes inside the capillary column which can be desorbed into a mobile phase for HPLC analysis. Instead of being chemically bonded, the wall coating inside the capillary is an unbound thin layer. The unbound solid phase poses some disadvantages for using SPME or conventional CME in HPLC analysis, including limited sorption, poor solvent stability, and thermal and pH instabilities. The use of varied mobile phases in HPLC makes it unsuitable to combine with SPME or CME and its thin layer wall coating.

To counteract shortcomings in combining CME with HPLC, sol-gel chemistry has been explored for coating the capillary for solid phase microextraction (SPME). The sol-gel technique can help minimize solvent and thermal effects on the coating. Sol-gel chemistry involves chemically bonding a (siloxane) polymer coating inside the capillary. As a result, various functional groups can be immobilized in the polymeric network for better extraction and improved sensitivity. Various silica and non-silica based coatings have been used in this approach. Apart from developing various new techniques in SPME, CME has its own uniqueness and advantages of being an online hyphenation with HPLC. CME is a simplified procedure with fewer variables to optimize and is more precise than other techniques having multiple parameters for one complete analysis. Several approaches to addressing these problems have been taken.

U.S. Pat. No. 7,622,191 to Malik et al. (Malik 191) discloses in situ preparation of a titania-based sol-gel PDMS coating and its immobilization on the inner surface of a fused silica microextraction capillary. Malik 191 uses a sol-gel titania-poly (dimethylsiloxane) ($TiO_2$-PDMS) coating for capillary microextraction (CME) to perform on-line preconcentration and HPLC analysis of trace impurities in aqueous samples. Malik 191 reports strong pH stability and enhanced extraction capability over commercially available GC coatings for its titania-based coatings, with extraction characteristics of a sol-gel titania-PDMS capillary practically unchanged after continuous rinsing with 0.1 M NaOH (pH=13) for 12 hours. However, Malik 191 requires a titanium, zirconium, and/or aluminum, particularly titanium, additive in its sol-gel, and fails to disclose yttria-containing sol-gels, much less a sol-gel formed from tris(hydroxyalkoxy) yttrium and/or [bis(hydroxyethyl)amine] (BHEA)-terminated polydimethylsiloxane.

CN 107091899 A by Yu et al. (Yu) discloses a tetrabromobisphenol A measuring method for environmental water. Yu's method involves: (1) pre-treating a water sample; (2) ageing the sample on a solid-phase microextraction fiber head; (3) soaking the solid-phase microextraction fiber head into the sample to separate and enrich target tetrabromobisphenol A; (4) inserting a SPME sampling needle into an SPME-HPLC interface; (5) performing dynamic desorption and completing separation and detection of chromatography-mass spectrometry. Yu's system, however, uses a conventional polydimethylsiloxane (PDMS) coating and does not describe any modifications of its PDMS, nor alternate materials.

EP 1 999 465 B1 to Gerhardt et al. (Gerhardt), which also published as WO 2007/112224 A2, describes an HPLC apparatus including a substrate that defines a separation column in fluidic communication with an inlet port of the processing unit. The processing unit is formed of sintered inorganic particles. The apparatus also includes a pump that delivers a solvent to the inlet port at a pressure sufficient for high-performance liquid-chromatography. Gerhardt describes yttria-stabilized zirconia as a high temperature co-fired ceramic, to provide higher pressure capability and fracture strength, which Gehardt uses to make an electrokinetic pump and glass particle frits from sintered inorganic particles. However, Gerhart does not describe a sol-gel formed from tris(hydroxyalkoxy) yttrium and/or BHEA-terminated PDMS, nor the use of such a sol-gel as a stationary phase in CME.

U.S. Pat. No. 9,006,354 to Otsuka et al. (Otsuka) discloses a method of manufacturing a composite composition, involving: bonding a dispersant to the surfaces of inorganic oxide particles to provide dispersibility in a hydrophobic solvent to the inorganic oxide particles, and then dispersing the inorganic oxide particles in a hydrophobic solvent; substituting the dispersant bonded to the inorganic oxide particle surfaces with a surface modifier, which is a polydimethylsiloxane-skeleton polymer having one functional group at one terminal end, in the hydrophobic solvent in which the organic oxide particles are dispersed to bond the functional group of the polydimethylsiloxane-skeleton polymer to the inorganic oxide particle surfaces; and conjugating a silicone resin and the inorganic oxide particles obtained in the previous step, wherein the surface thereof is modified by bonding the polydimethylsiloxane-skeleton polymer having one functional group at one terminal end, to obtain a composite composition. Otsuka's inorganic oxide particles may include oxides of zirconia (Zr), titanium (Ti), silicon (Si), aluminum (Al), iron (Fe), copper (Cu), zinc (Zn), yttrium (Y), niobium (Nb), molybdenum (Mo), indium (In), tin (Sn), tantalum (Ta), tungsten (W), lead (Pb), bismuth (Bi), cerium (Ce), antimony (Sb), and germanium (Ge), optionally with a surface modifying glycidyl polydimethylsiloxane (PDMS) with a molecular weight over 4400 g/mol. However, Otsuka does not use sol-gel chemistry, i.e., forms no sol-gel, and particularly no sol-gel formed from tris (hydroxyalkoxy) yttrium and/or BHEA-terminated PDMS. Moreover, Otsuka uses no such sol-gel as a stationary phase in CME.

CN 105542642 A by Shao et al. (Shao) describes a storage shelf comprising a metal shelf main body, wherein a surface of the metal shelf main body is coated with a metal protection coating. Shao's metal protection coating comprises, by weight, 1-2 parts of PDMS, 8.6 parts of polyurethane resin, 0.6 parts of sodium lauryl sulfate, 0.7 parts of petroleum sulfonate, 0.2 parts of $Al(OH)_3$, 0.2 parts of $Y_2O_3$, 0.8 parts of $Al_2O_3$, and 0.9 parts of 12-hydroxystearic acid. Shao uses its coating for rust resistance, corrosion resistance, oxidation resistance, and weatherability. Shao does not disclose sol-gels, nor using them a capillary or in CME, much less a sol-gel formed from tris(hydroxyalkoxy) yttrium and/or BHEA-terminated PDMS J. Chromatography A 2008, 1205(1-2), 26-35 by Sergo et al. (Sergo) discloses a sol-gel polydimethyldiphenylsiloxane (PDMDPS) coating for CME on-line hyphenated with HPLC. The coating uses methyltrimethoxysilane (MTMS) as the sol-gel precursor and di-hydroxy-terminated PDMDPS as the sol-gel active polymer. The methyl and phenyl groups on the sol-gel active polymer and the methyl groups on the sol-gel precursor are ultimately converted into pendant groups enabling extraction of non-polar analytes. A 40-cm segment of 0.25 mm I.D. fused silica capillary containing the sol-gel PDMDPS coating was installed as an external sampling loop in an HPLC injection port. Sample handling included passing aqueous samples through the capillary, and extracting analytes with the sol-gel coating. The extracted analytes were then transferred to the HPLC column using isocratic or gradient elution with an acetonitrile/water mobile phase. Sergo reports excellent extraction for non-polar, e.g., PAHs and aromatics, and moderately polar compounds, e.g., aromatic amines, ketones, and aldehydes. Sergo reports that PDMDPS can be immobilized into a sol-gel network and that the coating is high temperature solvent resistant and suitable for on-line hyphenation of CME with HPLC. However, Sergo does not disclose sol-gels comprising yttrium, polycondensed or otherwise, nor hydroxyalkylamine-terminated polysiloxanes, nor alkylaminoalkyl-moieties within its sol-gel.

Anal. Chem. 2007, 79(24), 9441-9451 by Fang et al. (Fang) describes germania-based, sol-gel hybrid organic-inorganic coatings for CME and GC. Fang reports that, as an isostructural analog of $SiO_2$, $GeO_2$ is compatible with the silica network, and germania-based materials possess great potential for being used in the areas of chromatographic separation and sample preparation. Fang's germania-based hybrid sol-gel material is used as a sorbent in analytical sample preparation or chromatographic separation. Tetramethoxygermane was used as a precursor to create a sol-gel network via hydrolytic polycondensation reactions performed within a fused-silica capillary. The growing sol-gel germania network was simultaneously reacted with an organic ligand that contained sol-gel-active sites in its chemical structure. Three different sol-gel-active ligands were used: (a) hydroxy-terminated PDMS; (b) hydroxy-terminated PDMDPS; and (c) 3-aminopropyltrimethoxysilane. Sol-gel germania-coated capillaries of desired polarity and extraction selectivity were prepared using an appropriately selected sol-gel-active ligand in the sol solution. These capillaries were further used to extract trace concentrations of PAHs, aldehydes, ketones, alcohols, phenols, and free fatty acids from aqueous samples, then analyze the extracts by GC-FID. Fang reports stability under harsh operation conditions involving extreme pH values, high temperatures, and aggressive solvents for the germania-based coatings, and potential as GC stationary phases. Fang does not, however, describe a yttria-based system, nor one using a hydroxyalkylaminoalkyl-terminated polysiloxane, and particularly no sol-gel formed from tris(hydroxyalkoxy) yttrium and/or BHEA-terminated PDMS.

J. Chromat. A. 2005, 1062(1), 1-14 by Alhooshani et al. (Alhooshani) discloses a zirconia-based hybrid organic-inorganic sol-gel coating for CME (in-tube SPME). Alhooshani reports that zirconia's chemical inertness makes it difficult to covalently bind a suitable organic ligand to its surface. Alhooshani uses sol-gel chemistry to chemically bind a hydroxy-terminated PDMDPS to a sol-gel zirconia network in the course of its evolution from a highly reactive alkoxide precursor undergoing controlled hydrolytic polycondensation reactions. A fused silica capillary was filled with a sol solution to allow sol-gel reactions to take place within the capillary for typically 15 to 30 minutes, chemically anchoring a layer of evolving hybrid organic-inorganic sol-gel polymer to the silanol groups on the inner capillary walls via condensation. The unbonded part of the sol solution was expelled from the capillary under helium pressure, leaving behind a chemically bonded sol-gel zirconia-PDMDPS coating on the inner walls. PAHs, ketones, and aldehydes were efficiently extracted and pre-concentrated from dilute aqueous samples using zirconia-PDMDPS sol-gel coated capillaries followed by thermal desorption and GC analysis of the extracted solutes. Alhoushani reports pH stability and retention of extraction characteristics intact after continuous rinsing with a 0.1 M NaOH solution for 24 hour for the hybrid zirconia sol-gel coatings. However, Alhooshani describe no yttria-containing system, nor one using a hydroxyalkylaminoalkyl-terminated polysiloxane, and particularly no sol-gel formed from tris(hydroxyalkoxy) yttrium and/or BHEA-terminated PDMS.

Coatings to date have been useful for a variety of purposes, but a need remains for new materials and coatings, as well as methods to make CTE and/or SPME more versatile.

SUMMARY OF THE INVENTION

Aspects of the invention provide sol-gels, comprising, in reacted form: a sol-gel precursor having a structure (I)

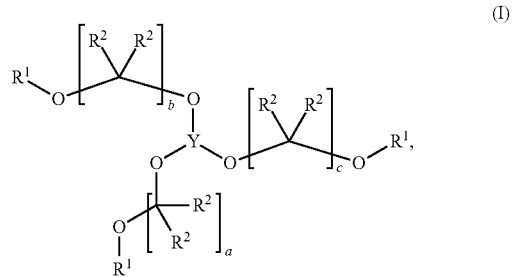

wherein R¹ may be independently H, methyl, ethyl, propyl, s-propyl, butyl, s-butyl, isobutyl, t-butyl, pentyl, s-pentyl, isoamyl, neopentyl, or C6-alkyl, R² may be independently H, methyl, ethyl, propyl, or F, and a, b, and c may be independently in a range of from 1 to 20; and a sol-gel active polymer having a structure (II)

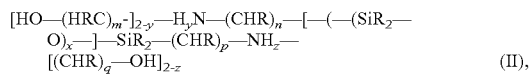

$$[HO-(HRC)_m-]_{2\text{-}y}-H_yN-(CHR)_n-[-(-(SiR_2-O)_x-]-SiR_2-(CHR)_p-NH_z-[(CHR)_q-OH]_{2\text{-}z} \quad (II),$$

wherein R may be independently H, methyl, ethyl, propyl, s-propyl, butyl, s-butyl, isobutyl, t-butyl, pentyl, s-pentyl, isoamyl, neopentyl, C6-alkyl, phenyl, or pyridyl, y and z may be independently 0 or 1, x may be in a range of from 5 to 2,500, and m, n, p, and q may be independently in a range of from 1 to 20. Such sol-gels may be modified with any permutation of features discussed herein.

In the sol-gel precursor, R¹ may be H, methyl, ethyl, or propyl, R² may be H, and a, b, and c may be in range of from 2 to 10. Additionally or separately, in the sol-gel precursor, a, b, and c may be identical and/or in a range of from 2 to 4.

In the sol-gel active polymer, R may be H, y and z may be 0, x may be in a range of from 25 to 500, and m, n, p, and q may be independently in range of from 2 to 10, and/or R may be H, y and z may be 0, x may be in a range of from 30 to 250, m and q may be identical, and m, n, and p may be independently in range of from 2 to 4. Additionally or separately, in the sol-gel active polymer, m and q may be identical to each other, n and p may be identical to each other, and m and n may be independently in range of from 2 to 5.

The sol-gel precursor may be may be self-condensed, to form a network comprising a poly-yttroxane, before condensation with the sol-gel active polymer. The sol-gel precursor may be hydrolyzed prior to self-condensation. Inventive coatings may have a contact angle with water in a range of from 70 to 100°.

The sol-gel may comprise termini comprising hydroxyalkyl groups. Useful sol-gel reagent ratios, based on "equivalents" of the sol-gel polymer to equivalents of the sol-gel precursor, may be in a range of from 1:2 to 1:10. Inventive sol-gels may be formed in a solvent comprising an alcohol in at least 50 wt. % of total solvent weight.

Inventive sol-gels may be those, wherein at least 90% of the sol-gel precursor comprises tris(methoxymethoxy) yttrium, tris(methoxyethoxy) yttrium, tris(ethoxyethoxy) yttrium, tris(methoxypropoxy) yttrium, tris(ethoxypropoxy) yttrium, tris(propoxypropoxy) yttrium, tris(methoxybutoxy) yttrium, tris(ethoxybutoxy) yttrium, tris(propoxybutoxy) yttrium, tris(butoxybutoxy) yttrium, tris(methoxypentanoxy) yttrium, tris(ethoxypentanoxy) yttrium, tris(propoxypentanoxy) yttrium, and/or tris(butoxypentanoxy) yttrium, and wherein at least 90% of the sol-gel active polymer comprises [HO—(H₂C)₂]₂—N—(CH₂)₂—[—(Si(CH₃)₂—O)₃₀₋₅₀]—Si(CH₃)₂—(CH₂)₂—N[(CH₂)₂OH]₂, [HO—(H₂C₃]₂—N—(CH₂)₂—[—(Si(CH₃)₂—O)₃₀₋₅₀]—Si(CH₃)₂—(CH₂)₂—N[(CH₂)₃OH]₂, [HO—(H₂C₂]₂—N—(CH₂)₃—[—(Si(CH₃)₂—O)₃₀₋₅₀]—Si(CH₃)₂—(CH₂)₃—N[(CH₂)₂OH]₂, [HO—(H₂C)₃]₂—N—(CH₂)₃—[—(Si(CH₃)₂—O)₃₀₋₅₀]—Si(CH₃)₂—(CH₂)₃—N[(CH₂)₃OH]₂, [HO—(H₂C)₂]₂—N—(CH₂)₄—[—(Si(CH₃)₂—O)₃₀₋₅₀]—Si(CH₃)₂—(CH₂)₄—N[(CH₂)₂OH]₂, [HO—(H₂C₄]₂—N—(CH₂)₂—[—(Si(CH₃)₂—O)₃₀₋₅₀]—Si(CH₃)₂—(CH₂)₂—N[(CH₂)₄OH]₂, [HO—(H₂C)₃]₂—N—(CH₂)₄—[—(Si(CH₃)₂—O)₃₀₋₅₀]—Si(CH₃)₂—(CH₂)₄—N[(CH₂)₃OH]₂, [HO—(H₂C₄]₂—N—(CH₂)₃—[—(Si(CH₃)₂—O)₃₀₋₅₀]—Si(CH₃)₂—(CH₂)₃—N[(CH₂)₄OH]₂, and/or [HO—(H₂C₄]₂—N—(CH₂)₄—[—(Si(CH₃)₂—O)₃₀₋₅₀]—Si(CH₃)₂—(CH₂)₄—N[(CH₂)₄OH]₂. Inventive sol-gels may be formed by reacting monomers comprising yttrium methoxyethoxide (YMEO) and [bis(hydroxyethyl)amine] (BHEA)-terminated polydimethylsiloxane.

Aspects of the invention may include hybrid organic-inorganic materials, which may comprise a glass having a glass surface comprising silanol moieties; and any inventive sol-gel(s) described herein, terminal hydroxyl groups of the sol-gel active polymer are condensed with the silanol moieties of the glass surface to form a covalent bond having the substructure [glass]-Si—[O—(HRC)m-]₂-y-HyN—(CHR)n-[—(SiR₂—O)x-]..., wherein [glass] is a glass matrix, and —Si—[O— represents an interface of one of the silanol moieties, condensed with a hydroxyl group of the sol-gel. Such glass surfaces may be those of capillaries, comprising inner surface(s) that may be coated with any inventive sol-gel described herein, generally covalently bonded thereto. Such capillaries may be fused silica micro-extraction capillaries, particularly of Type I fused silica.

Aspects of the invention include micro extraction methods, which may comprise: (a) introducing a dissolved sample into a capillary coated and/or covalently bonded with any inventive sol-gel described herein; and optionally (b) passing an eluant comprising acetonitrile and/or deionized water through the capillary. Aspects of the invention include methods for analyzing samples, which methods may comprise: (a) introducing a diluted sample or a dissolved sample into a capillary coated and/or covalently bonded with any inventive sol-gel described herein; (b) passing an eluant through the capillary; (c) desorbing an extracted analyte from the capillary onto an analytical column; and (d) eluting the analytical column. Aspects of the invention include methods of enhancing analytical sensitivity, comprising: combining a capillary coated and/or covalently bonded with any inventive sol-gel described herein in series with an HPLC or GC column.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 17A is before exposing the inventive capillary to acid/base conditions; FIG. 17B is after exposing the inventive capillary to 1.0 M NaOH for 24 hours; and FIG. 17C is after exposing the inventive capillary to 1.0 M HCl for 24 hours.

DETAILED DESCRIPTION OF THE PREFERRED EMBODIMENTS

Figure 1:
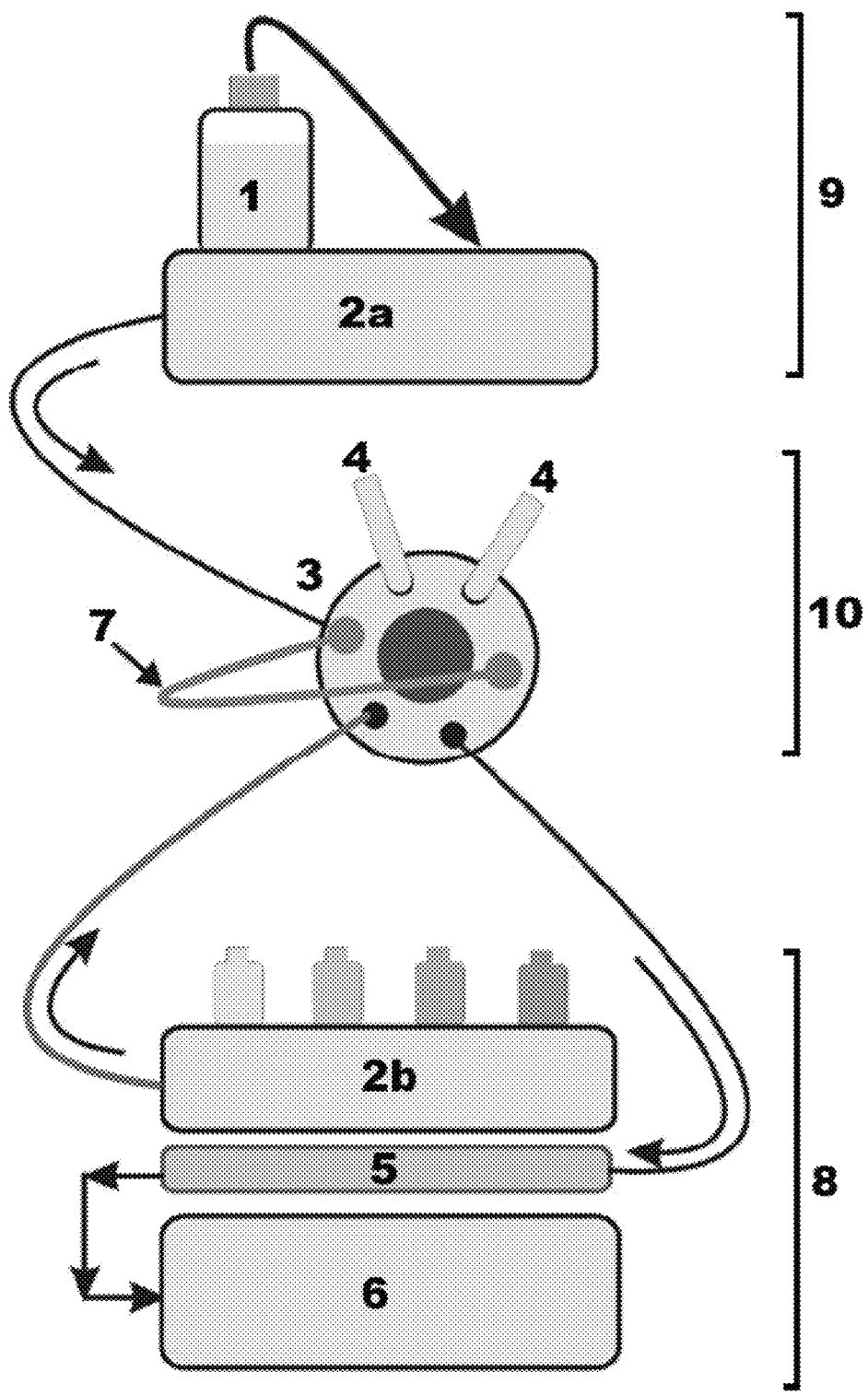
FIG. 1 shows a representation of the setup for CME-HPLC online analysis using the sol-gel within the scope of the invention.

Aspects of the invention provide sol-gels formed from bis(hydroxyalkyl)amine-terminated poly-dialkyl/aryl siloxane(s), such as [bis(hydroxyethyl)amine] (BHEA)-terminated polydimethylsiloxane (PDMS), and yttrium alkoxy-alkoxide(s), such as yttrium methoxyethoxide. Such sol-gels, e.g., BHEA-Y sol-gel, can be used as surface immobilized coatings for capillary microextraction. Such materials can have remarkable extraction sensitivity for compounds of varied polarities, non-polar to highly polar, in online CME-HPLC for analytes including well established environmental pollutants. Toxins and persistent environmental pollutants subject to analysis with such coatings may include PAHs, alcohols, aldehydes, ketones, amides, and phenols. For example, phenols may arise from the synthesis of pesticides, dyes, explosives, and drugs in various industries. The hydroxyl group of phenols may react with disinfection by-products and form chlorinated phenols with higher toxicity. Nitrite may react with phenol in environmental water to form more toxic and persistent nitrophenols. These hazards of the phenols make its pre-concentration and real sample analysis e.g., by CME, an interesting application of inventive coatings.

Aspects of the invention provide sol-gels, comprising, in reacted form: a sol-gel precursor having a structure (I)

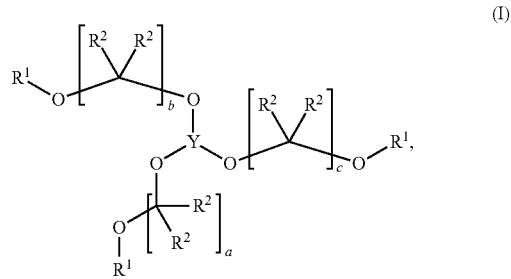

wherein $R^1$ is independently H, methyl, ethyl, propyl, s-propyl, butyl, s-butyl, isobutyl, t-butyl, pentyl, s-pentyl, isoamyl, neopentyl, or C6-alkyl, $R^2$ is independently H, methyl, ethyl, propyl, or F, and a, b, and c are independently in a range of from 1 to 20, 1 to 18, 1 to 16, 1 to 14, 2 to 10, 2 to 6, 2 to 4, etc., wherein the carbons are preferably unsubstituted and generally selected to be hydrolyzable as kinetically and/or thermally desired, while not uncontrollably self-condensing; and a sol-gel active polymer having a structure (II)

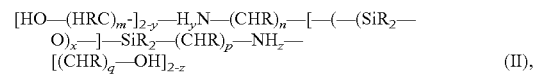

wherein R independently may be H, methyl, ethyl, propyl, s-propyl, butyl, s-butyl, isobutyl, t-butyl, pentyl, s-pentyl, isoamyl, neopentyl, C6-alkyl, phenyl, or pyridyl, y and z may be independently 0 or 1, x may be in a range of from 5 to 2,500, or at least 10, 20, 25, 28, 30, 32, or 34, and m, n, p, and q may be independently in a range of from 1 to 20, or independently any of 2, 3, 4, 5, 6, 7, 8, 9, 10, 11, 12, 13, 14, or 15. The alkylene spacers between the amine and the polysiloxane in the sol-gel active polymers and/or between the oxygens in the sol-gel precursors could preferably be ethylene, propylene, or butylenes.

Suitable sol-gel precursors include tris(methoxymethoxy) yttrium, tris(methoxyethoxy) yttrium, tris(ethoxyethoxy) yttrium, tris(methoxypropoxy) yttrium, tris(ethoxypropoxy) yttrium, tris(propoxypropoxy) yttrium, tris(methoxybutoxy) yttrium, tris(ethoxybutoxy) yttrium, tris(propoxybutoxy) yttrium, tris(butoxybutoxy) yttrium, tris(methoxypentanoxy) yttrium, tris(ethoxypentanoxy) yttrium, tris(propoxypentanoxy) yttrium, tris(butoxypentanoxy) yttrium, etc. The "glycol" may be spaced by essentially any alkylene group having the necessary solubility for the end application, e.g., C1 to C25, C2 to C15, or the like, such as C2, C3, C4, C5, C6, C7, . . . C25. The "spacer" may likewise be a PEG or PPG, or less regular polyether or ether element of similar or even longer chain lengths (given the improved solubility), e.g., up to C100, C75, C50, or C30. The length of the alkylene group may be balanced with the effect of the alkyl cap, which may be similarly unlimited, so long as the elements are collectively hydrolyzable under reaction conditions. The alkyl spacers between the glycol oxygens, may be interrupted by one or more oxygens (forming ethers), and/or may be substituted, e.g., with 1, 2, 3, or 4 methyl, ethyl, propyl, fluoro, carboxylate, methoxy, ethoxy, and/or hydroxy groups (or be perfluorinated), but need not be. The sol-gel precursor(s) can be made to undergo a controlled polycondensation to form the colloidal system called sol and this sol further form a 3D structure that is called gel. In the polycondensation reaction shown at the bottom of FIG. 2, the number of silanol to sol-gel active polymer may be 1, 2 or 3, preferably 2, per chain.

Inventive sol-gels could advantageously employ 2, 3, 4, or even 5 or more sol-gel active polymers and/or sol-gel precursors. Inventive sol-gel active polymers generally have $M_v$ in a range of from 1000 to 10,000, 2,000 to 7,500, 2,500 to 5,000, 2,750 to 4,250, or 3,000 to 4,000. For practical synthetic reasons, in the sol-gel active polymer(s) and/or sol-gel precursor(s), a and b, m and q, and/or n and p may be identical to each other. Moreover, certain applications may preferably avoid aryl substituents on the polysiloxane backbone. As a consequence of the reaction of the sol-gel precursor with the sol-gel active polymer, the sol-gel precursor may "cap" or terminate the sol-gel active polymer.

The sol-gel precursor(s) may be reacted with at least one sol-gel active polymer, e.g., polydialkylsiloxane, polydiarylsiloxane, polyarylalkylsiloxane, polyhydroalkylsiloxane, polyhydroarylsiloxane, etc., such as polydimethylsiloxane (PDMS), polydiethylsiloxane (PDES), polydipropylsiloxane, polymethylethylsiloxane, polymethylphenylsiloxane, polydiphenylsiloxane (PDPS), copolymers, and terpolymers thereof, capped by hydroxyalkyl aminoalkyl groups. In Formula (II), y and z may independently be 0 or 1, preferably 0; x may be in a range of from 5 to 2,500, 10 to 1,500, 15 to 1,000, 20 to 750, 25 to 500, 30 to 250, or 35 to 100; and m, n, p, and q may independently be 2, 3, 4, 5, 6, 7, 8, 9, 10, 12, 14, 16, or more, as long as the necessary solubility and reactivity are retained. Exemplary terminal moieties on any of the above described or otherwise known sol-gel active polymers, i.e., backbone(s), include bis(hydroxyethyl)amine (BHEA), bis(hydroxypropyl)amine, bis(hydroxybutyl)amine, bis(hydroxypentyl)amine, and bis(hydroxyhexyl)amine. Any intervening alkyl spacers between the amine terminus and the polysiloxane may be used, so long as the necessary solubility and reactivity are retained, including 1, 2, 3, 4, 5, 6, 7, 8, 9, 10, or more carbons, which may be interrupted by one or more oxygens (forming ethers), and/or may be substituted, e.g., with 1, 2, 3, or 4 methyl, ethyl, propyl, fluoro, carboxylate, methoxy, ethoxy, and/or hydroxy groups (or be perfluorinated).

The sol-gel precursor may be self-condensed, to form a network comprising a poly-yttroxane, before condensation with the sol-gel active polymer. That is, there may be a plurality of —O—Y—O—Y—O— structures, generally cross-linked into an interconnected network, containing the yttrium atoms in a volume, bonded to the hydroxyalkylaminoalkyl-terminated polysiloxane(s), which may be further bonded to silanol group(s) on the surface of glass or similar materials. The sol-gel precursor may be hydrolyzed prior to self-condensation, i.e., presented in a stabilized hydrolyzed form, or hydrolyzed, then self-condensed. Essentially, the yttrium may be polycondensed into a network from a form of $Y(OH)_3$.

Inventive coatings may have a contact angle with water in a range of from 70 to 100, 75 to 95, 80 to 90, 82.5 to 87.5, or 84 to 86°. Inventive coatings will generally be more hydrophobic than coatings, particularly yttrium-based coatings, excluding the hydroxyalkylaminoalkyl-terminated polysiloxane(s). Inventive coatings may cover at least 50, 60, 70, 75, 80, 85, 90, 95, 99, 99.9, or 100% of the interior surface of a capillary. Inventive coatings may sufficient to maintain at least 75, 80, 92.5, 95, 97.5, 98, 99, 99.1, 99.5, or 99.9%, of their sensitizing efficiency—i.e., improvement in LOD over CME-free HPLC, after 12, 24, 48, 72, or 96 hours, or 5-7 days or 2, 3, or 4 weeks at pH 0 and/or 14.

The sol-gel precursor may be pre-condensed before condensation with the sol-gel active polymer, preferably using a chelating agent comprising acetic acid, citric acid, malonic acid, oxalic acid, trifluoroacetic acid, methanesulfonic acid, toluenesulfonic acid, benzenesulfonic acid, triflic acid, hydrochloric acid, hydrobromic acid, hydroiodic acid, and/or sulfuric acid, in at least 75, 80, 92.5, 95, 97.5, 98, 99, 99.1, 99.5, or 99.9 wt. %, based on total chelating agent weight. The chelating agent may have a pKa (in water) of less than 1, 0.75, 0.5, 0.25, or −0.25.

The sol-gel may comprise termini comprising hydroxyalkyl groups, particularly 2, 3, 4, or more per chain. Useful sol-gel reagent ratios, based on "equivalents" of the sol-gel polymer (insofar as "moles" can be estimated based on $M_v$, $M_w$, and/or $M_n$) to equivalents of the sol-gel precursor, may be in a range of from 1:2 to 1:20, 1:15, 1:10, 1:9, 1:8, 1:7, or 1:6. Inventive sol-gels may be formed in a solvent comprising water and/or an alcohol, particularly methanol, ethanol, n-propanol, and/or isopropanol, in at least 50, 60, 70, 75, 80, 85, 90, 95, 97.5, 98, 99, 99.1, 99.5, or 99.9 wt. % of total solvent weight. The sol-gel active polymer(s) and/or precursors can be dissolved in a solvent, for example water, methanol, ethanol, propanol, isopropanol, butanol, THF, dioxane, ethylene glycol, diethyl ether, dischloromethane, chloroform, pyridine, acetone, and/or ethyl acetate, to dissolve the contents in the sol solution. The hydrolyzed reactive species may further undergo polycondensation to produce an yttria-comprising three-dimensional network.

Aspects of the invention may include hybrid organic-inorganic materials, which may comprise a glass having a glass surface comprising silanol moieties; and any inventive sol-gel(s) described herein, terminal hydroxyl groups of the sol-gel active polymer are condensed with the silanol moieties of the glass surface to form a covalent bond having the substructure [glass]-Si—[O—(HRC)$_m$-]$_{2-y}$—H$_y$N—(CHR)$_n$—[—(SiR$_2$—O)$_x$—] . . . . This expression represents the glass matrix as "[glass]" and the glass surface silanol, covalently bonded to a chain in the glass matrix, as "—Si—[O—," whereby the "O" represents a post-condensation shared oxygen between the end of the sol-gel (i.e., sol-gel active polymer(s)). Such covalent bonds between the glass surface and the sol-gel may be 1, 2, 3, or 4 bonds per chain, preferably 2. Such glass surfaces may be (micro)capillaries, comprising inner surface(s) that may be coated with any inventive sol-gel, and may be fused silica micro-extraction capillaries.

Lengths of the capillaries may be in a range of from 10 cm to 15 m, 15 cm to 10 m, 25 cm to 5 m, 30 cm to 3 m, or the like, depending upon the application, e.g., at least 50 cm, 75 cm, 1 m, 2 m, or more. Exemplary inner capillary diameters may be 100 to 1000, 150 to 750, 200 to 500, or 250 to 400 microns, and/or at least 2, 5, 10, 15, 20, 25, 30, 40, 45, 50, 60, 75, 100, 115, 125, 140, 150, 180, 200, 220, 250, 280, 320, 430, 450, 530, 680, or 700 microns, and/or no more than 800, 725, 700, 690, 630, 550, 500, or 450. Outer diameters of useful capillaries may be at least 50, 90, 100, 150, 180, 200, 230, 250, 280, 300, 315, 350, 380, 400, 425, 450, 475, 500, 550, or 600 micron, and/or no more than 1000, 950, 900, 880, 850, 825, 700, 660, 625, 575, 550, 525, 500, 475, 465, 435, 415, 390, or 365 microns. Capillaries may also have inner diameters in a range of from 2 to 5, 2.1 to 4, 2.2 to 3, or 2.3 to 2.7 mm. Inventive capillaries may be made of or comprise (e.g., at least 75, 80, 85, 90, 91, 92, 92.5, 93, 94, 95, 96, 97, 97.5, 98, 99, 99.1, 99.5, or 99.9 wt. % of a total weight of the capillary material) fused silica, optionally with a polyimide coating. The fused silica may include Type I, Type II, Type III, and/or Type IV.

Capillaries having inventive coatings may be loaded with a pump and/or gas (e.g., He, $N_2$, Ar, etc.) pressure. Typical flow ranges into and/or out of the capillary may be in a range of from 1 to 20,000, 2 to 10,000, 5 to 5,000, 10 to 2,500, 15 to 2,00, 25 to 1,500, or 50 to 1000 μL/min, and/or at least 5, 10, 40, 75, 100, 150, 250, 500, 750, or 800 μL/min, and/or no more than 15,000, 12,500, 7,500, 6,000, 4,000, 3,000, 2,250, 1,750, 1,250, 1,000, or 950 μL/min. The analytes may be desorbed with a pump, such as a ChromatoProbe pump (Aviv Analytical Ltd.), which lead directly into an HPLC, GC, and/or GC-MS.

Preparations of inventive sol-gels may involve vortexing at 5,000 to 20,000, 7,500 to 17,500, 10,000 to 15,000, 12,500 to 14,000, or 13,000 to 13,500 rpm, or at least 9,000, 11,000, 12,000, or 12,750 rpm, for at least 5, 6, 7, 8, 9, 10, or 15 minutes, and/or no more than 30, 25, 20, 15, 12, 11, or 10 minutes, to give a pre-cured sol-gel, and the sol-gel may be cured at a temperature in a range of from 150 to 350, 175 to 325, 200 to 310, or 250 to 300° C., under an inert environment. The solvent in which the sol-gel is formed can impact the morphology of the product. Ethanol, methanol, and/or propanol may be useful for many applications, particularly ethanol alone or ethanol/propanol (1:1, 1:2, 1:3, 2:3, or 2:1 mixtures), or either of these may be exchanged for water, or the solvent may be 50, 60, 70, 80, 90, 95, 99, or 100 wt. % water. In addition to the sol-gel precursor(s), sol-gel active polymer(s), and chelates, additives may be included in the reaction mixture, such as tri-alkoxyalkylsilane(s)—e.g., trimethoxymethylsilane, triethoxyethylsilane, trimethoxyphenylsilane, etc.—in an amount of up to 20, 15, 10, 5, 2.5, 2, 1, 0.5, 0.1, or 0.001 wt. %, relative to total sol-gel "monomer" weight, to increase cross-linking.

Inventive (micro)extraction methods, may comprise: (a) introducing an aqueous or otherwise dissolved sample into a capillary coated and/or covalently bonded with any inventive sol-gel described herein; and optionally (b) passing an eluant, e.g., comprising acetonitrile, THF, methanol, and/or (deionized) water, through the capillary. Inventive coatings may have thickness in a range of from 0.5 to 20, 1 to 18, 2 to 16, 3 to 15, 4 to 12.5, 5 to 11, 6 to 10, or 7 to 9 microns, though, in other applications, the coatings may be at least 1.25, 1.67, 2.33, 2.5, 2.67, 3, 3.25, 3.5, 4, 5, 7.5, 10, 15, or 25 microns, and/or no more than 50, 40, 33, 30, 25, 20, 17.5, 16.7, 13.3, 12.5, or 10 microns. The non-hydrogen mass composition of inventive sol-gels may be 10 to 40, 15 to 38, 20 to 30, or roughly 25 wt. % carbon; 0.5 to 10, 0.75 to 7.5, 0.9 to 5, 1 to 2.5, 1.05 to 1.5, or roughly 1 wt. % nitrogen; 15 to 75, 20 to 60, 25 to 57.5, 30 to 55, 35 to 52.5, or roughly 49 wt. % oxygen, 10 to 30, 12.5 to 27.5, 15 to 25, 17.5 to 24, 18 to 24, 20 to 22, or roughly 21.5 wt. % silicon, and/or 0.05 to 10, 0.1 to 8, 0.2 to 6, 0.5 to 5, or 1 to 4, or roughly 3.4 wt. % yttrium ("roughly" meaning ±0.1, 0.25, 0.5, 0.75, 1, or 1.5 wt. %). Non-C/N/O/Si/Y/H elements in inventive sol-gels will generally represent no more than 10, 5, 2.5, 2, 1, 0.5, or 0.1 wt. % in total.

Sensitivities of detection methods/devices may be increased 1.5, 2, 3, 5, 7.5, 10, 12.5, 15, or even 20-fold, by including an inventively coated capillary prior to the hyphenated follow-on analytical method, versus the analytical method alone.

Inventive sol-gels may comprise no more than 10, 5, 4, 3, 2, 1, 0.5, 0.1, 0.001, 0.0001, or 0.00001 wt. %, relative to the total inorganic polymer weight, of titanium, aluminum, germanium, zirconium, iron, copper, zinc, niobium, molybdenum, indium, tin, tantalum, tungsten, lead, bismuth, cerium, and/or antimony. Inventive sol-gels may comprise no more than 10, 5, 4, 3, 2, 1, 0.5, 0.1, 0.001, 0.0001, or 0.00001 wt. %, relative to the total organic polymer weight, of aromatic moieties, such as phenyl(ene) and/or naphthyl(ene) groups. Inventive sol-gel active polymers may comprise no more than 40, 33, 25, 20, 15, 10, 7.5, 5, 4, 3, 2, 1, or 0.5 wt. %, relative to the total sol-gel active polymer weight, of methyltrimethoxysilane (MTMS) and/or polydimethyldiphenylsiloxane (PDMDPS). Inventive siloxanes may comprise at least 75, 80, 85, 90, 91, 92, 92.5, 93, 94, 95, 96, 97, 97.5, 98, 99, 99.1, 99.5, or 99.9%, based on count of (dialkyl)siloxane monomers, of methyl and/or ethyl substituents, i.e., —$(Si(CH_3)_2—O)_n$—.

Aspects of the invention include applications of inventive coatings in online CME-HPLC, CME-GC, CME-LC, CME-MPLC, CME-LC-MS, etc., analysis for polar and/or nonpolar analytes. Exemplary CME parameters are shown in Table 1, below.

TABLE 1

Typical CME parameters and associated ranges

| GC-MS parameters for CME devices | Range (typical) |
|---|---|
| Inlet liner | 1 to 5 or 2 to 4 mm (2 mm) ultra-inert split/splitless gooseneck |
| Inlet temp | 200 to 300, 220 to 280, 225 to 275, or 245 to 265° C. (260° C.) |
| Carrier gas | Helium, Argon, and/or $N_2$ |
| Pressure | 10 to 20, 12 to 18, 13 to 17, or 14 to 15 psi (14.49 psi) |
| Average velocity | 30 to 60, 40 to 55, 45 to 52.5, or 47.5 to 50 cm/s (49.76 cm/s) |
| Column | 10 to 40 m × 100 to 500 mm × 0.1 to 0.5 mm (30 m × 250 mm × 0.25 mm) |
| Oven temp | 25-50° C., 1-5 min, 10-50° C./min, 30-60° C., 100-300° C., 1-5 min (30° C., 2.5 min, 40° C./min, 260° C., 2.5 min) |
| Source temp | 100 to 300° C. (230° C.) |
| Transfer line temp | 100 to 300° C. (280° C.) |

Example

EQUIPMENT: An HPLC system (Agilent Technologies, USA) equipped with a quaternary pump (G1311B/C), a DAD (G4212B), with manual injection port, an analytical column Agilent ZORBAX Eclipse XDB C-18 (5 μm, 4.6 mm id×250 mm), and Chemstation software were used. An Agilent 1260 Infinity isocratic pump (G13103B) was also utilized for sample flow through the coated capillary. For the preparation and homogenized mixing of (BHEA-Y) sol, Thermofisher Scientific MaxiMix Vortex mixer was used (model M16715). A Sorvall™ Legend™ micro17 Microcentrifuge was used to settle the precipitates in the sol-solution. X-ray photoelectron spectroscopy (XPS) analysis of the BHEA-Y coating was conducted on Thermo Scientific ESCALAB 250Xi (PHI 5000 Versa Probe II, ULVAC-PHI Inc., UK) to determine the bonding state and surface chemical composition. Before analysis, a chunk of the polymer sample was mounted on carbon tape and subjected to high vacuum to remove impurities or moisture adsorbed on the sample. Thermal stability and decomposition of BHEA-Y coating were observed by thermogravimetric analysis (TGA) using an SDT Q600, V20.9 Build 20, thermal analyzer (USA) under nitrogen (N$_2$) environment from 30 to 600° C. with the constant heating rate of 10° C./minute. The morphological information of the BHEA-Y coated in capillary fused silica was examined by field emission scanning electron microscope (FE-SEM) from TESCAN, LYRA 3 (Czech Republic), using secondary electron (SE) and back-scattered electron (BSE) mode at an accelerating voltage of 30 kV and equipped with energy dispersive x-ray spectrometer (EDS, Oxford Inc.) detector for elemental analysis. The polarity of the surface material was determined from contact angle calculations with water using an Attention theta optical tensiometer, C204A, (Biolin scientific, Finland), equipped with one-attention software (version 3.2, r5971).

CHEMICALS AND MATERIALS: Fused silica capillaries (320 μm I.D.) were purchased from Polymicro Technologies USA. Yttrium methoxyethoxide (YMEO, CAS NO: 115668-57-0, 314.17 g/mol, d~1.01 g/mL) and [bis (hydroxyethyl)amine] (BHEA)-terminated polydimethylsiloxane (CAS NO: 2024596-86-7, 3000 g/mol, 120-160 cSt, d~0.97 g/mL) were purchased from Gelest, USA. 4-bromoacetanilide, N-methyl-1-naphthylacetamide, benzanilide, 4-fluorophenol, 2,3-dichlorophenol, 2,4-dichlorophenol, 2,4,6-trichlorophenol, 2-benzyl-4-chlorophenol, pentachlorophenol, 4-tert-octylphenol, 2-naphthol, 1-naphthol, diphenylcarbinol, 5,5-dimethyl-1,3-cyclohexadione, 1,2-naphthoquinone, 1-indanone, 4-methoxyacetophenone, 4-hydroxybenzophenone, 2-hydroxy-2-phenylacetophenone, propiophenone, benzophenone, benzil, 4-chlorobenzophenone, 4-hydroxy-3-methoxybenzaldehyde, 5-nitrosalisaldehyde, 4-chlorobenzaldehyde, 5-bromobenzaldehyde, naphthalene, biphenyl, fluorene, phenanthrene, and anthracene were purchased from Sigma-Aldrich USA.

PREPARATION OF SOL-SOLUTION: A sol-solution was prepared by vortexing a sol-gel active polymer BHEA (200 μL, 0.194 g, ~0.0647 mmol, 1 eq.) with 200 μL ethanol in a microcentrifuge tube for 30 seconds. The sol-gel active precursor YMEO (100 μL, 0.101 g, 0.321 mmol, 4.96 eq.) and 8.0 μL water were added to the reaction mixture and vortex for 90 seconds. The sol-solution was then ready for the coating inside the fused silica microextraction capillary.

PREPARATION OF A BHEA-Y SOL-GEL COATED MICROEXTRACTION CAPILLARY: A 3.0 m long fused silica capillary (320 μm i.d.) was rinsed with methanol and dichloromethane and pretreated with a 1.0 M NaOH solution. The 1.0 M NaOH solution was kept inside the capillary for 2 hours, by closing both ends of the capillary, and then flushed. The capillary was rinsed with 0.1 M HCl to neutralize any NaOH present and later then rinsed with water. All the rinsing and etching procedures were done under helium pressure using an in-house built gas pressure-operated capillary filling device. The capillary was then kept inside the GC oven for drying at 250° C. overnight under helium flow and thereafter taken out of GC and installed into an in-house built gas pressure-operated capillary filling device for rinsing with methanol and dichloromethane before coating.

A 1.0 m long piece of the pretreated capillary was used for sol-gel coating using a gas pressure operated purging device. The sol solution was pressured into the capillary and kept inside the capillary for 10 minutes to enhance the on-surface reaction of the sol coating. The unreacted sol solution was then expelled out of the capillary using helium gas pressure, and the helium flow was continued for 10 additional minutes. The coated capillary was then subjected to a post-treatment as described in *J. Chromat. A.* 2004, 1047, 165-174 (incorporated herein by reference in its entirety), using the GC oven to make the sol-gel material more porous and clean.

ONLINE CAPILLARY MICROEXTRACTION (CME) AND HPLC ANALYSIS: The online CME-HPLC analytical system used in the example is presented in FIG. 1, including a sample flow system (9), manual injection port (10), and an HPLC system (8). In an exemplary run, the analytical column (5) was pre-equilibrated with the mobile phase and kept ready for manual injection. A 40 cm long BHEA-Y sol-gel coated capillary (7) was fixed in place of the sample loop in the manual injection port (3). The injection port (3) was switched to "load" mode and an aqueous sample (1) having the analytes of interest was pre-concentrated in the BHEA-Y sol-gel coated capillary (7) with a constant flow of 1.0 mL/min using the isocratic pump (2a). Deionized water was later flushed through the BHEA-Y sol-gel coated capillary (7) to remove the sample present inside the capillary loop. The injection port (3) was then switched to "inject" mode for the desorption of the extracted analytes from the BHEA-Y sol-gel coated capillary (7) to the analytical column (5). Using a gradient pump (2b), the analytical column (5) separated the analytes based on the interaction between mobile phase and stationary phase and the analytes were detected with a UV detector (6).

EXTRACTION COMPARISON OF YTTRIA BASED COATING AND BHEA-Y BASED COATING: The extraction performance of the capillary coated with yttria (alone) and capillary coated with an exemplary inventive sol-gel, comprising a BHEA-Y sol-gel, was compared. For the preparation of yttria-based coating, the sol-solution was prepared exactly as in the case of BHEA-Y, as described above, excluding the addition of BHEA. To support the extraction results, contact angles were determined to analyze the hydrophobicity or hydrophilicity of the coatings. The yttria sol-gel based coating was also characterized by field emission scanning electron microscopy (FE SEM) and energy-dispersive x-ray spectroscopy (EDS). A specific run was designed containing one member from a variety of compound classes and diode array detection with varied absorption wavelengths for relevant compound classes was used. The variables were kept constant and extraction was tested in triplicate.

ANALYSIS OF THE ANALYTES WITH VARIOUS POLARITIES: Using this complete extraction and analysis procedure with the selected BHEA-Y coated capillary, compounds ranging in various polarities were tested for extraction ability, enrichment factors, and detection limits. The enrichment factors were calculated by dividing the peak area of the extracted analyte by the peak area of standard analyte, as described in *Anal. Chem.* 2011, 83, 7531-7541 (incorporated herein by reference in its entirety). The peak area for the analyte from the standard solution was obtained by injecting 20 μL of the standard solution into the HPLC manual port without any extraction. Various classes of compounds include amides, phenols, alcohols, ketone, aldehyde, and polyaromatic hydrocarbons were tested. The limit of detection of all the analytes was calculated by signal to noise ratio (S/N=3).

Beyond testing the extraction ability of the coated capillary, the solvent and chemical stability of the coating material was also tested. For this purpose, extreme pH environments were applied to the coated capillary for 24 hours. The coated capillaries were continuously rinsed using 1.0 M HCl (pH=0) and NaOH (pH=14) for 24 hours and then tested for the extraction of the analytes (each member from the various compound classes). The BHEA-Y coated capillary was also tested for preparation method reproducibility. Three capillaries were prepared, keeping all the synthesis and coating factors identical, and installed into the online CME-HPLC system to compare the extraction efficiency of the analytes.

METHOD VALIDATION AND REAL SAMPLE ANALYSIS OF PHENOLS: Aspects of the invention test new sorbent surface materials for the extraction of analytes having different polarities. Any chromatographic method, particularly those well-developed and validated methods, may be applied for the analytes in, e.g., aqueous samples. Phenols, a polar class of compounds and well-known environmental pollutants, were selected for the analytical method validation. Some of the analytical tools which may be considered include calibration curve, linear regression coefficient, limit of detection (LOD), limit of quantification (LOQ), inter-day and intra-day precision, and capillary to capillary precision. The calibration curves were plotted using concentrations of 5, 10, 25, 50, 100, 200, and 400 ng/mL versus peak area. A linear trendline model was applied and linear regression equations and constant were calculated. LOD and LOQ were calculated using a signal to noise ratio method. The reproducibility of the results (or precision) was calculated statistically from the ratio of standard regression error to data mean, and the ratio was converted to percentage. Inter-day, intra-day, and capillary to capillary precision were evaluated by repeating the analysis thrice (n=3).

To evaluate the applicability of the method to real samples, wastewater and swimming pool-water samples were collected and analyzed using BHEA-Y coated capillary for online CME-HPLC analysis of phenols. The samples were filtered using 4.5-micron membrane filter paper. The filtered samples were then passed through the capillary for extraction and HPLC analysis to analyze the presence of phenols in the sample. The real samples were also assessed for recovery and precision by spiking with three concentrations (5, 50, and 200 ng/mL) from the linear range.

CHEMICAL ANCHORING OF BHEA-Y BASED SOL-GEL COATING: An exemplary sol-gel precursor, yttrium methoxyethoxide (YMEO), and an exemplary sol-gel active polymer, [bis(hydroxyethyl)amine] (BHEA)-terminated polydimethylsiloxane, can undergo a hydrolysis and polycondensation to form the colloidal system called a sol. A solvent, particularly an alcohol, such as ethanol, can dissolve the contents of the sol solution. The hydrolyzed reactive species can further undergo polycondensation reactions to produce an yttria-based three-dimensional network.

Figure 2:
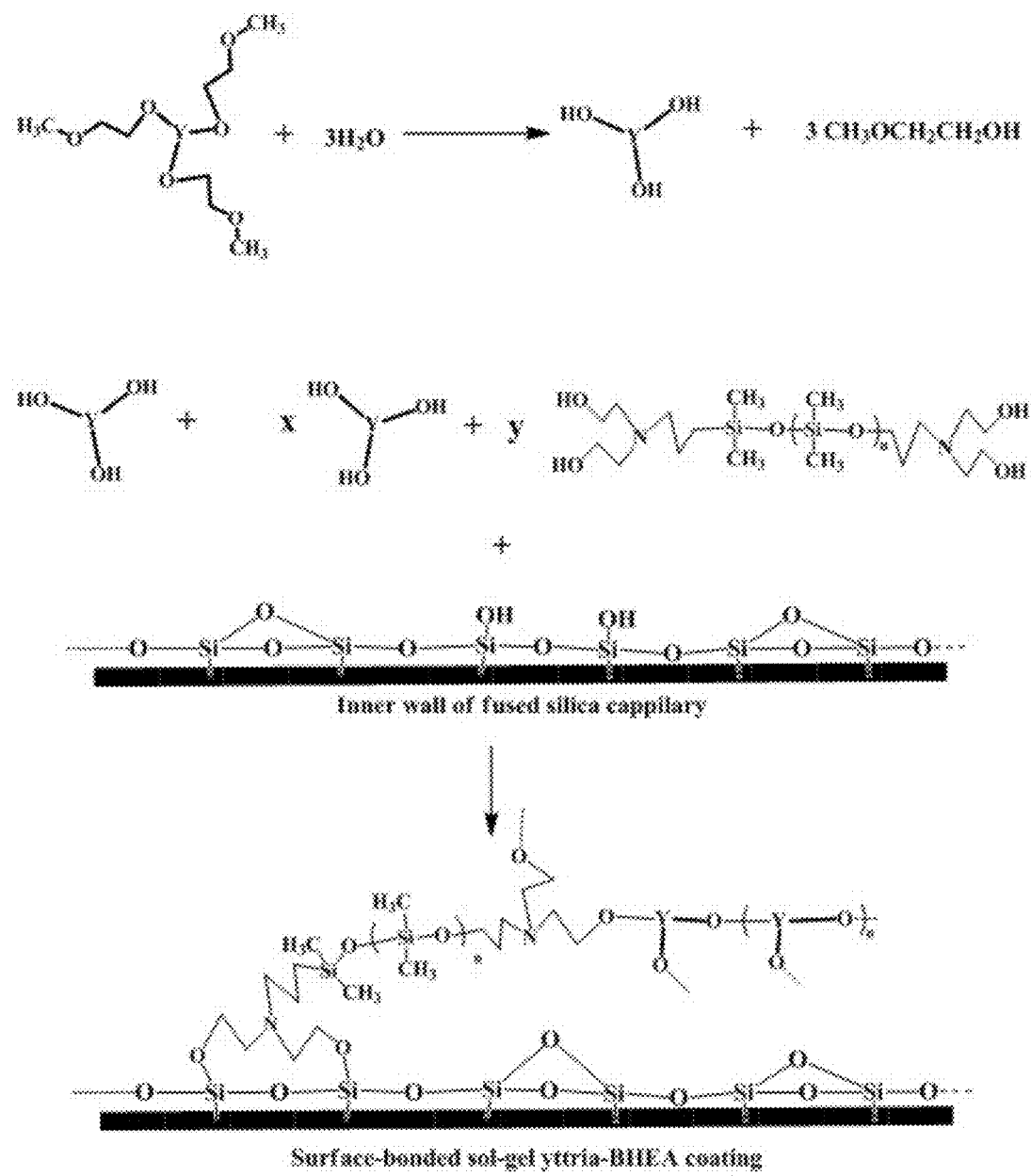
FIG. 2 shows a reaction scheme representing the hydrolysis of yttrium trimethoxyethoxide, a polycondensation of hydrolyzed yttrium hydroxide, and an exemplary final structure of a poly-yttroxane-bis-[(hydroxyethyl)amine] (BHEA)-terminated polydimethylsiloxane (BHEA-Y) coating within the scope of the invention.

A sol-gel active polymer with appropriate end groups, such as BHEA, can undergo condensation reaction with the silanol groups on the inner side of the fused silica capillary and produce a surface bonded polymer with sol-gel active precursor, forming yttria network over the surface. Later, heat treatment of such a coated capillary can cross-link the polymer, thereby enhancing the porosity. Overall, the sol-gel process for creating yttria-based coating(s) involves: (i) hydrolysis of the sol-gel precursor(s), yttrium alkoxyalkoxide(s), e.g., methoxyethoxide, precursor; (ii) polycondensation of the sol-gel precursor, e.g., YMEO, to form an yttria-based sol-gel network after the hydrolysis; (iii) polycondensation of the sol-gel active polymer(s), e.g., BHEA, with the yttria sol-gel network(s); and (iv) chemical immobilization of the sol-gel material(s), e.g., BHEA-Y sol-gel, to the silanol groups on a glass or other hydroxyl-containing surface, such as inner surface(s) of fused silica capillaries. This general sol-gel process creates an yttria-based sol-gel, surface bonded coating useful, e.g., for microextraction. FIG. 2 represents the hydrolysis, polycondensation of the YMEO precursor, and anchoring of the final coating material network inside the capillary wall.

Figure 4A:
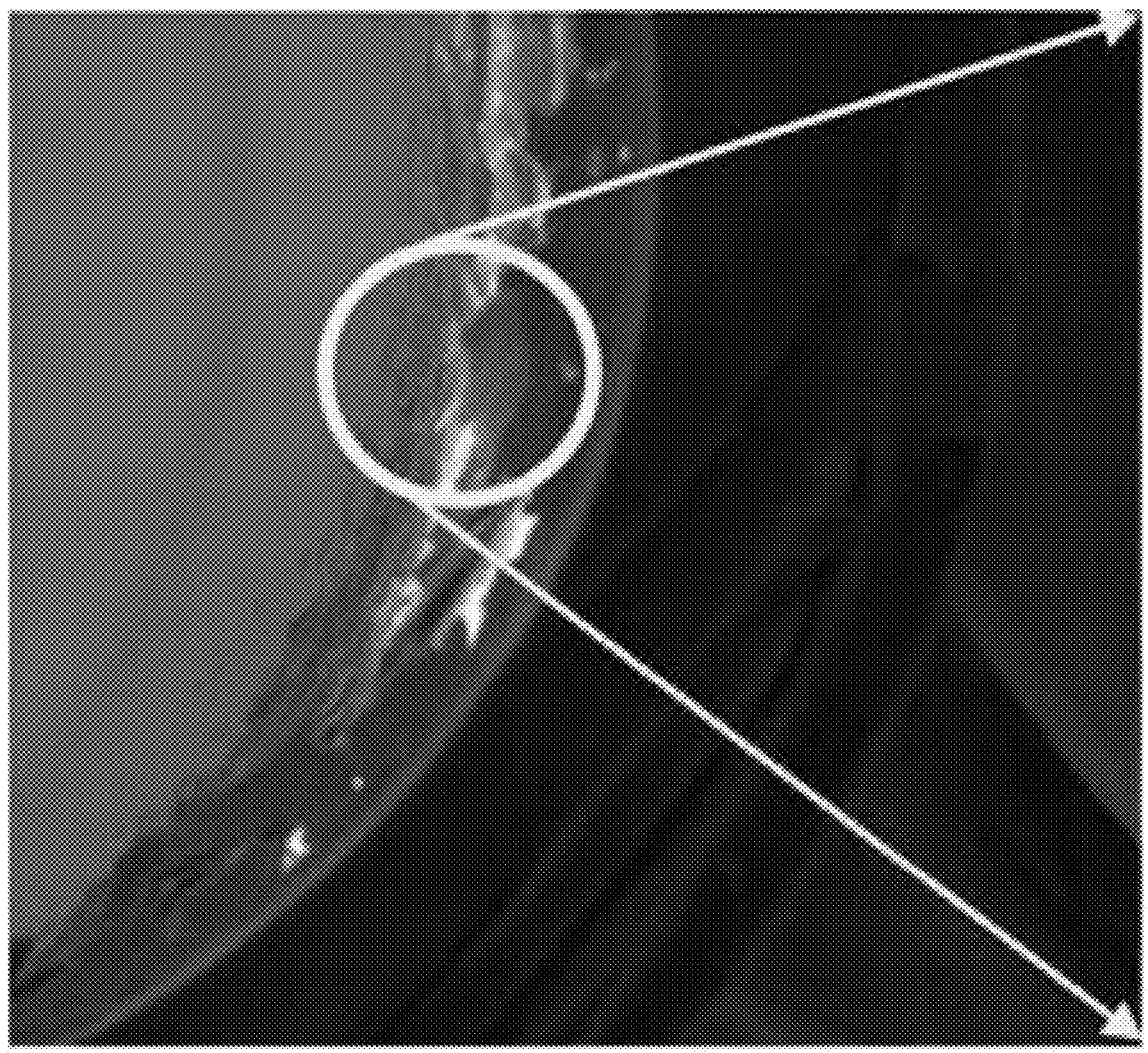
FIGS. 4A and 4B show SEM analysis of an yttrium oxide coating according to the invention inside the fused silica capillary at low (FIG. 4A) and high (FIG. 4B) magnifications, with an inset in FIG. 4B showing the thickness of hybrid polymer coated in capillary fused-silica.
Figure 4B:
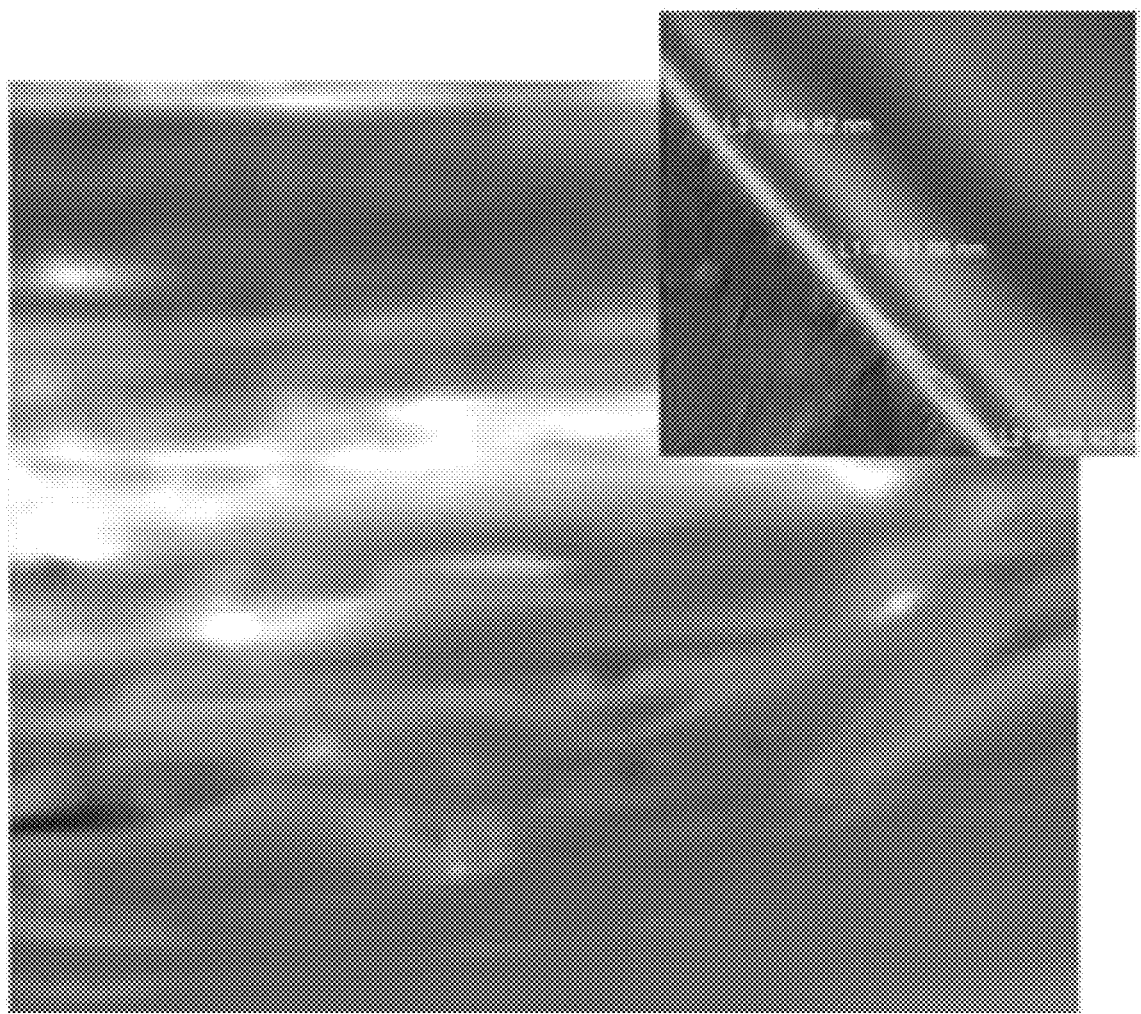
Figure 5:
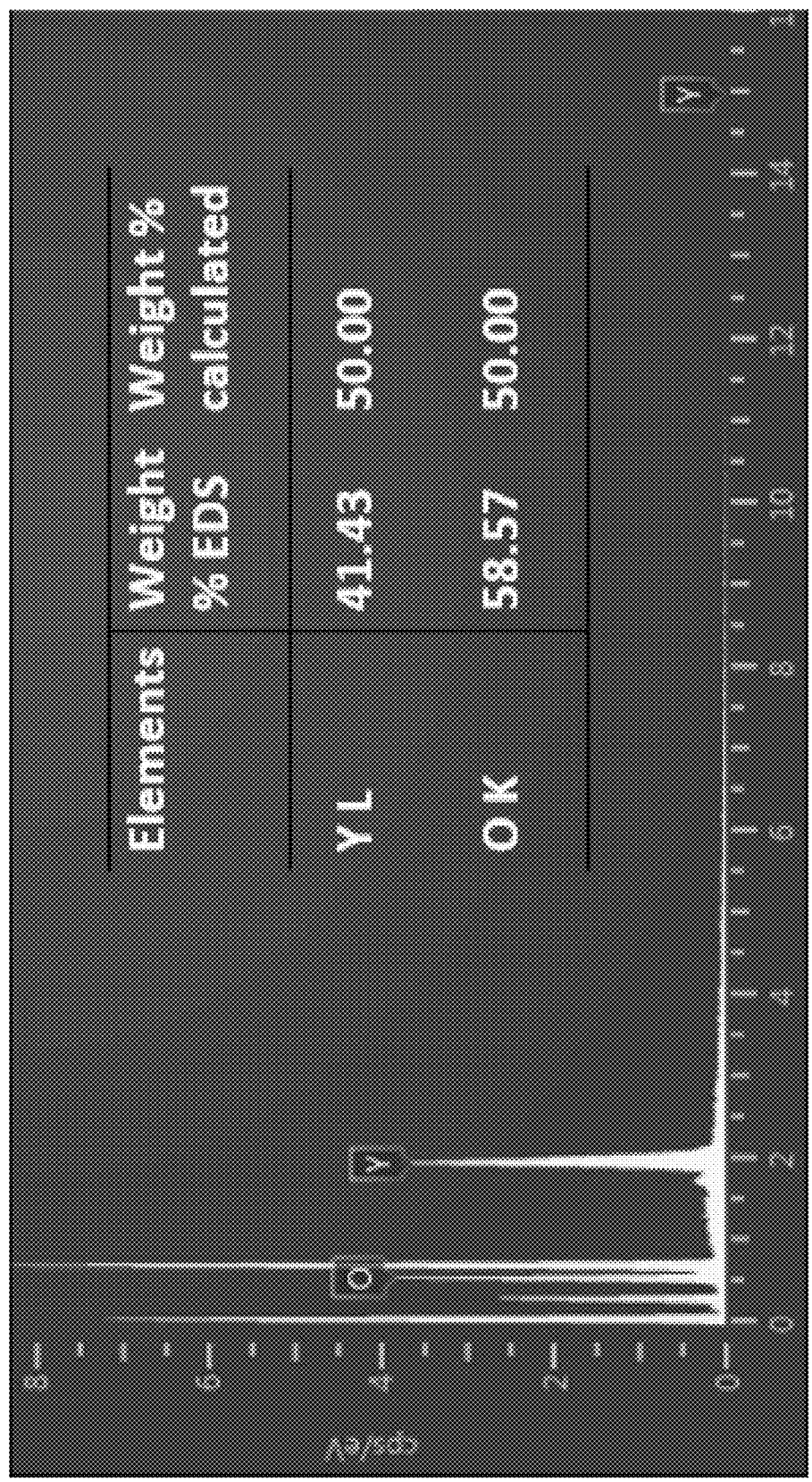
FIG. 5 shows energy dispersive x-ray spectroscopy (EDS) analysis of an yttrium oxide polymer, coated inside a fused-silica capillary, and the inset table presents atomic weight (%) fractions.
Figure 6A:
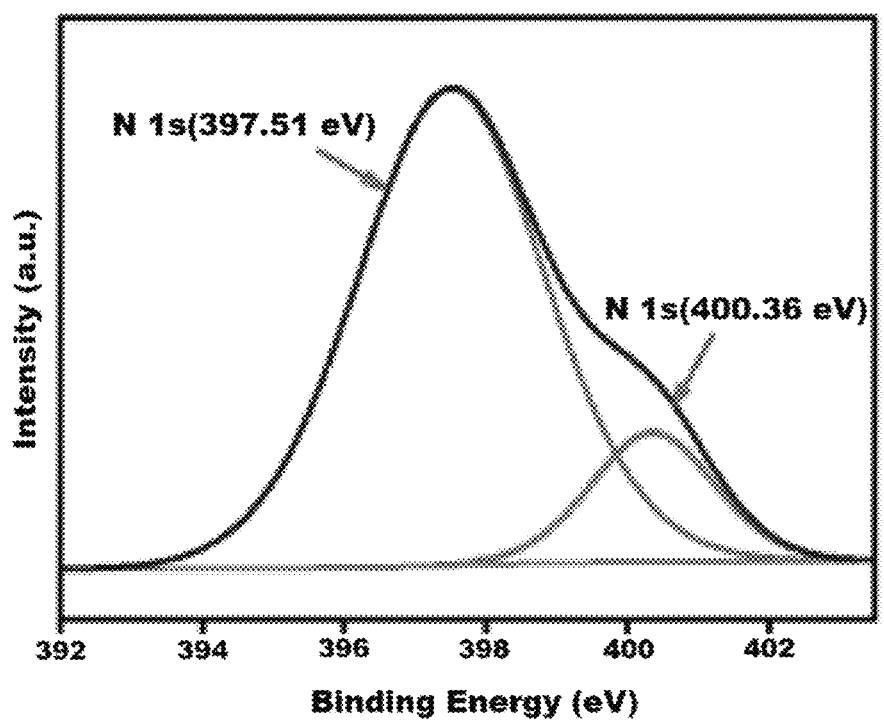
FIG. 6A to 6E show x-ray photoelectron spectroscopy (XPS) analyses showing different bonding states of Y, C, N, O and Si of a BHEA-Y polymer according to the invention, synthesized as described herein, before coating a fused-silica capillary.
Figure 6B:
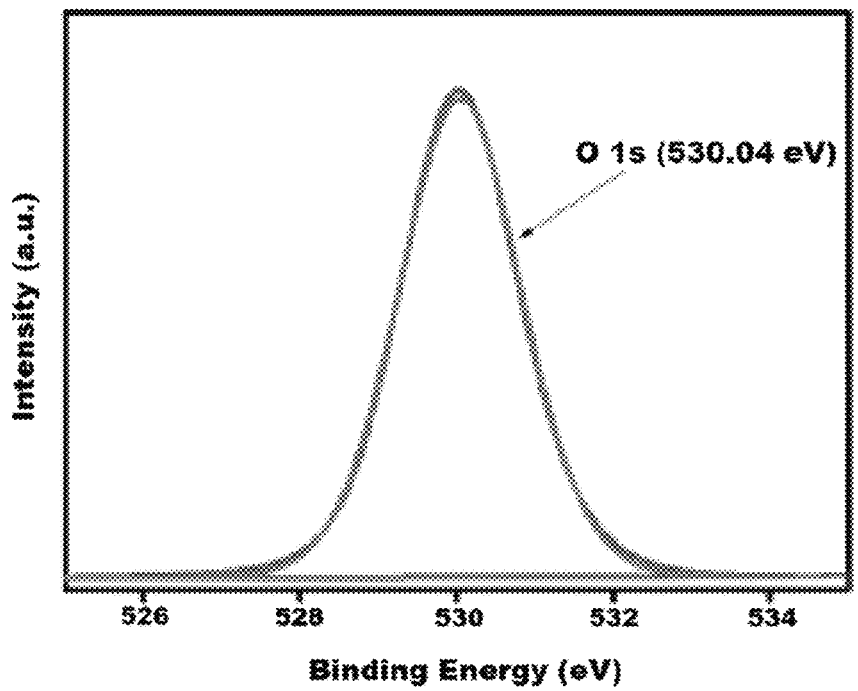
Figure 6C:
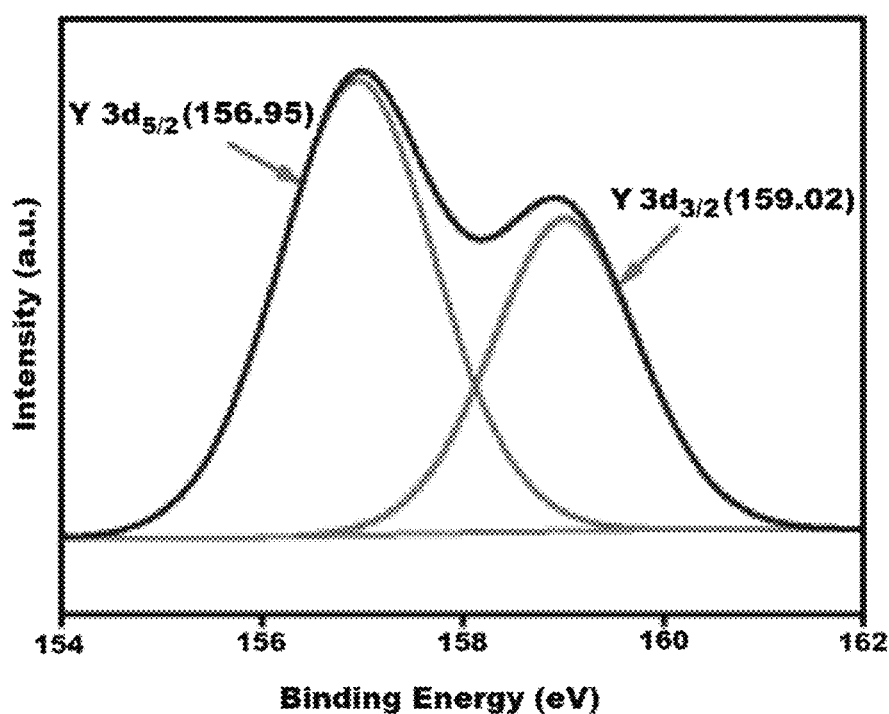
Figure 6D:
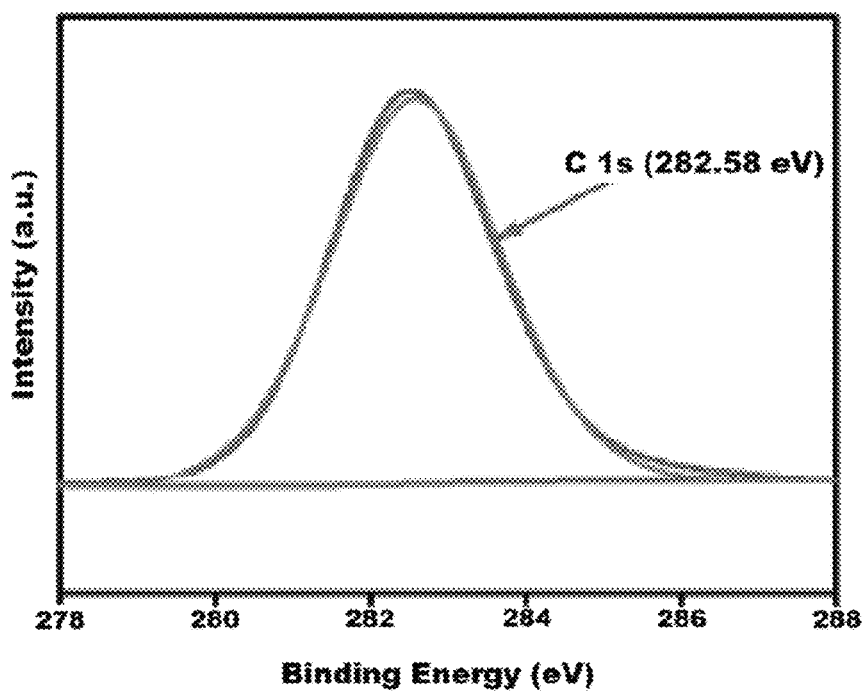
Figure 6E:
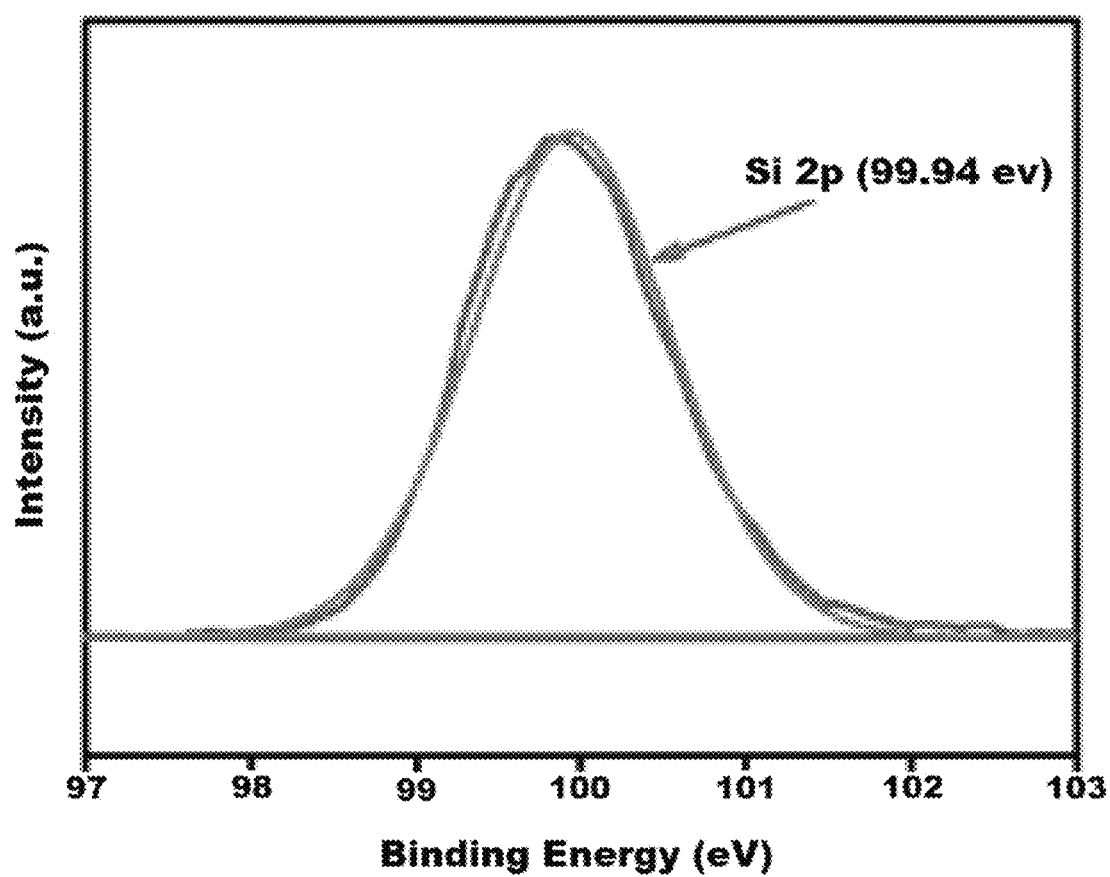

YTTRIA BASED COATING VERSUS BHEA-Y BASED COATING: Two capillaries were prepared, one with a BHEA-Y polymer backbone and one with Y, but without BHEA polymer, and the extraction was compared in FIG. 3A (BHEA-Y-based) versus FIG. 3B (Y-based). The prepared coating without BHEA polymer was characterized using FE SEM, as shown in FIG. 4A and FIG. 4B, and energy dispersive x-ray spectroscopy (EDS) of a yttrium oxide coating is shown in FIG. 5. The characterization results evidence successful chemical immobilization of yttrium oxide inside the capillary. The extraction results show that the BHEA-Y based coating extracted all classes of the analytes 10-15 times better than yttria alone, which was an unexpected result. Without wishing to be bound to theory, it is believed that the superior results may derive from the BHEA polymer providing more sorbent surface and a non-polar moiety.

A sol-solution of the BHEA-Y coating and a sol-solution of the yttria coating were applied to glass slides to form a thin layer. These glass slides were used to determine the contact angles of the coated surfaces with water. The yttria-based coating showed higher hydrophilicity, with a contact angle was 67.309°, and the BHEA-Y coating showed less hydrophilicity, with contact angle to 85.478°. The BHEA-Y based coating provided an overall hydrophilic surface, better extraction, and an ability to extract analytes of various polarities.

CHARACTERIZATION OF THE BHEA-Y SOL-GEL COATING FOR CME: A sol-gel derived polymeric yttria material/sample/adsorbent (BHEA-Y) was analyzed by x-ray photoelectron spectroscopy (XPS). The XPS analysis reveals the presence of carbon, nitrogen, oxygen, silicon, and yttrium. The peak deconvolution of each constituent gives quantitative information about the surface percentage with respect to their binding energies (BE) and oxidation states. FIG. 6 presents an XPS spectrum of BHEA-Y, with carbon (C 1s) representing the major component (approximately 57%) found at binding energy of 282.58 eV. AC 1s signal at this binding energy corresponds to carbon bonded with silicon and nitrogen atoms. Oxygen (O 1s) was observed at a binding energy of 530.04 eV, corresponding to an oxygen attached to a metal and silicon, with 21.73% surface atomic percent. Evidence of the presence of silicon (17.86%) was found at binding energy of 99.94 eV, corresponding to Si 2p attached to oxygen and carbon atoms. The XPS spectrum reveals two forms of nitrogen at 397.51 and 400.36 eV, corresponding to N 1s in nitride-form in two different environments, with a total N surface concentration of less than 1%. Similarly, yttrium was observed in low concentration as compared to C, Si, and O. Yttrium bonding states for $3d_{5/2}$ and $3d_{3/2}$ spin orbitals were observed as respective yttria binding energies of 156.95 and 159.02 eV. The atomic surface percent of yttrium with respect to other constituents of the BHEA-Y sol-gel was found to be 2.67%, using a binding energy of 156.95 eV for a $3d_{5/2}$ spin orbital as see below in Table 2. The observed elemental analysis with corresponding bonding energies of BHEA-Y confirms the successful attachment of yttria on BHEA through sol-gel synthesis, suitable for extraction applications.

TABLE 2

The bonding states and atomic weight
(%) of polymer composition by XPS

| Name | Peak BE | Atomic % |
|---|---|---|
| O1s | 530.04 | 21.73 |
| Si2p | 99.94 | 17.86 |
| Y3d$_{5/2}$ | 156.95 | 2.63 |
| N1s | 397.51 | 0.68 |
| N1s | 400.36 | 0.12 |
| C1s | 282.58 | 56.99 |

Figure 8A:
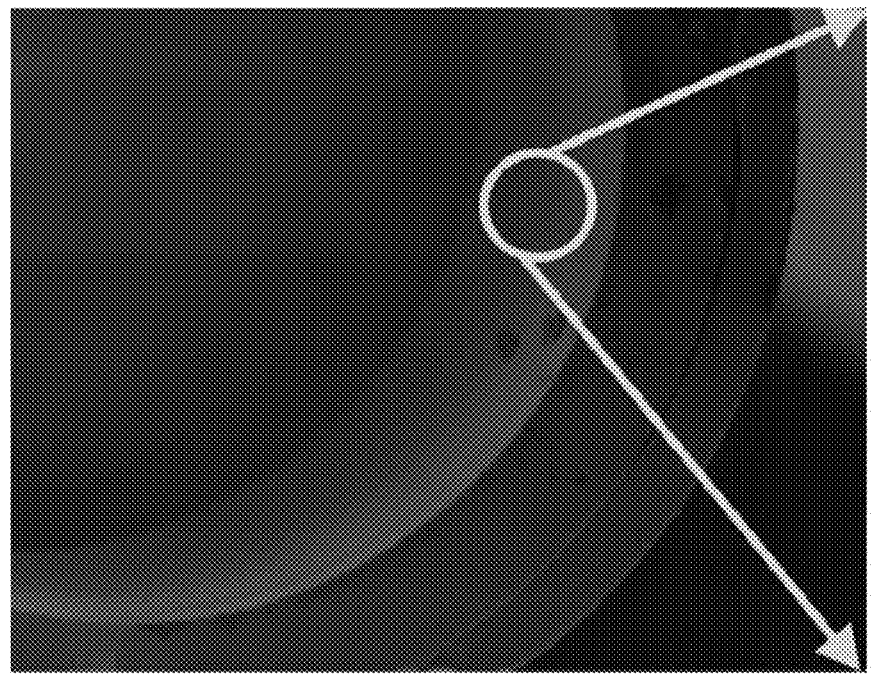
FIGS. 8A and 8B show scanning electron microscopy (SEM) images of a BHEA-Y polymer coating according to the invention, inside a fused silica capillary at low (FIG. 8A) and high (FIG. 8B) magnifications, with an in FIG. 8B showing the thickness of the coating within the fused-silica capillary.
Figure 8B:
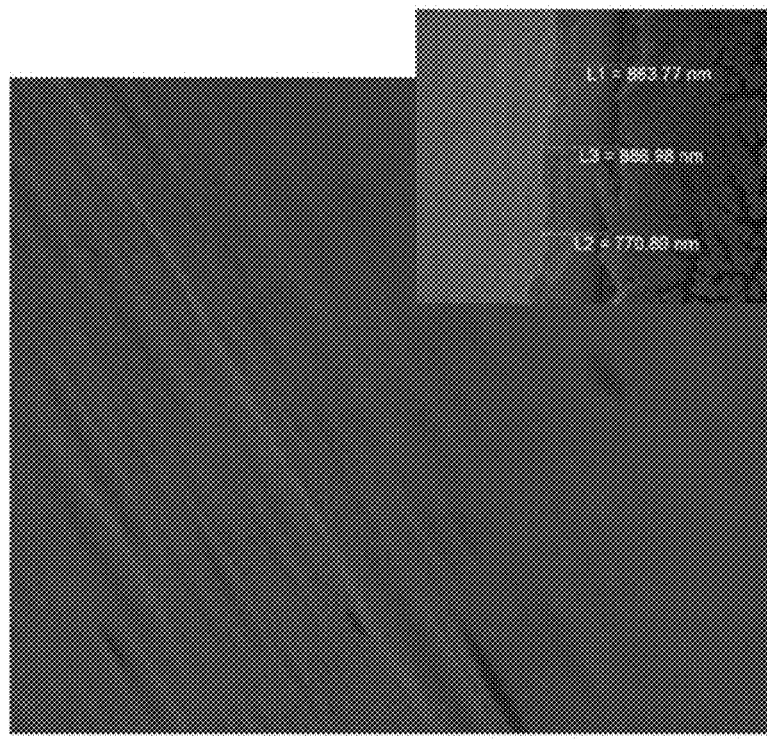
Figure 9:
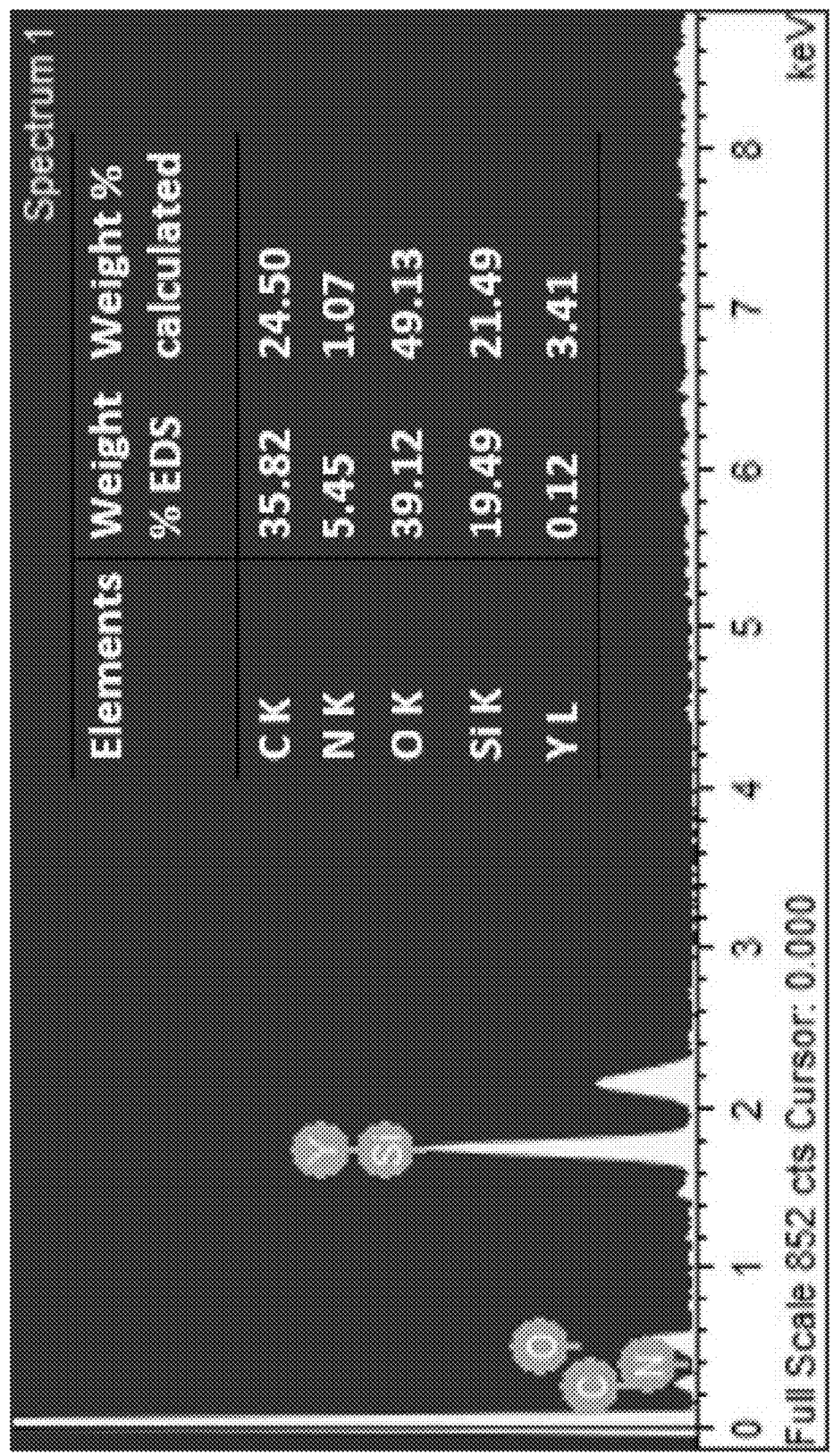
FIG. 9 shows an EDS analysis of a BHEA-Y polymer coating according to the invention, coated inside a fused-silica capillary with an inset table presenting atomic weight (%) fractions.

Successful BHEA-Y sol-gel polymer coating inside the capillary was observed by scanning electron microscope (SEM) at high resolution, as shown in FIG. 8A and FIG. 8B, and by energy dispersive spectroscopy (EDS) in FIG. 9.

Figure 10:
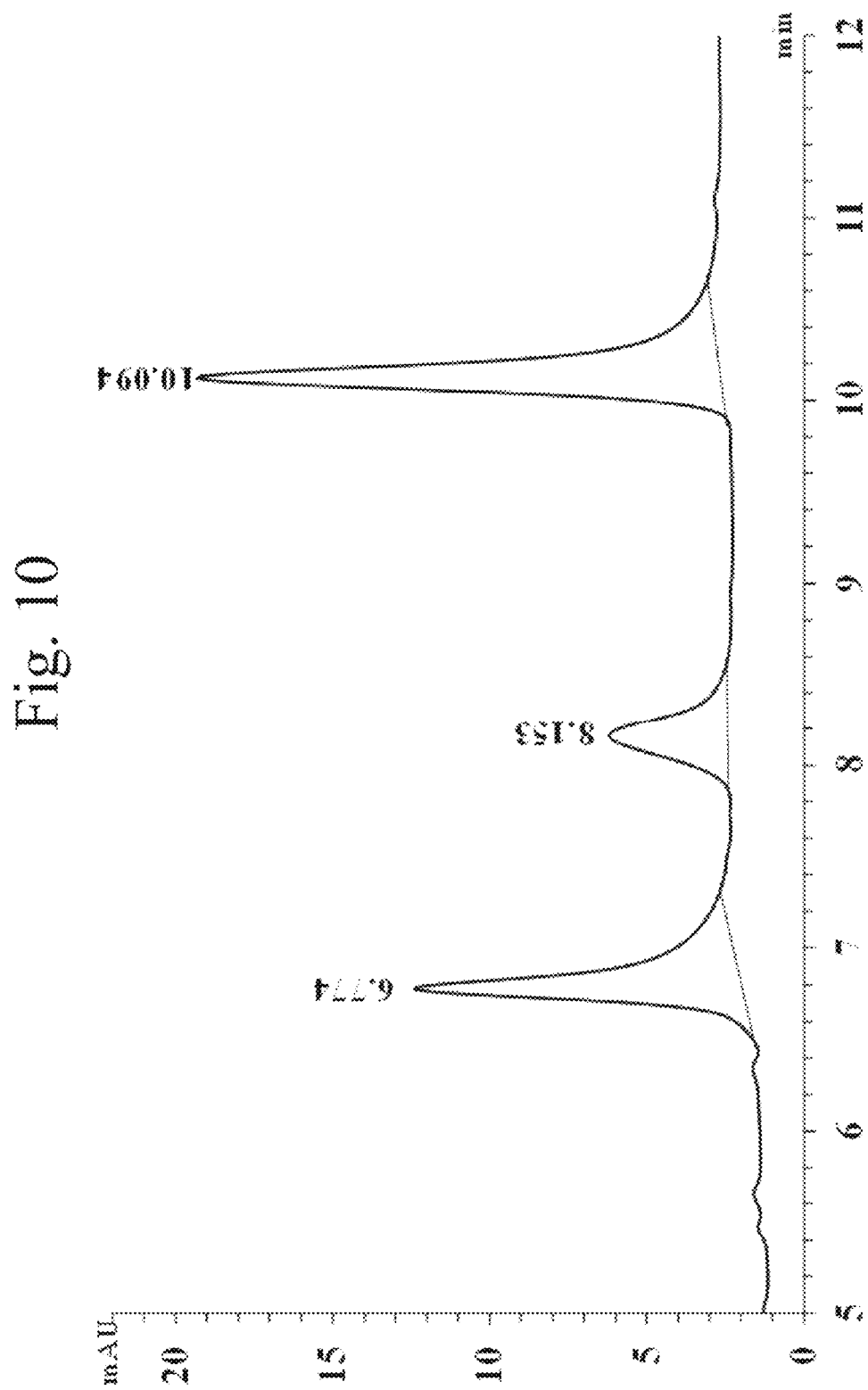
FIG. 10 shows a capillary microextraction (CME)-HPLC analysis of amides using a coated capillary within the scope of the invention.

ONLINE CME-HPLC ANALYSIS USING SOL-GEL COATED BHEA-Y CAPILLARY: Excellent extraction efficiencies were achieved for diverse compound classes, ranging from non-polar to highly polar compounds, using BHEA-Y based coatings inside a capillary. The selected analyte classes include the polyaromatic hydrocarbons (PAHs), aldehydes, ketones, alcohols, phenols, and amides. The BHEA-Y coated capillary presented exceptional ability to be equally suitable for the polar analyte and the non-polar analyte. Extraction of non-polar analytes is believed to be due to the presence polydimethylsiloxane (PDMS), or similar, portions in the BHEA sol-gel active polymer, while polar analytes were presumably efficiently extracted due to hydrophilic yttrium oxide moiety over the polymeric surface. Amides are considered to be polar analytes, and thus, were selected to test the ability of BHEA-Y coated capillaries for extracting highly polar analytes. Online CME-HPLC analysis of amides was successfully conducted using BHEA-Y based coated capillaries as shown in FIG. 10. The amides analyzed had enrichment factors (78.9 to 153.6), low detection limits ranging between 2.60 to 5.95 ng/mL (S/N=3) and reliable relative standard deviation (% RSD) of less than 6.1%) where n was 3, as shown in Table 3, below.

TABLE 3

Peak area reproducibility and detection limits for amides, phenols, alcohols, ketones, aldehydes, and PAHs in CME-HPLC[a] using a sol-gel BHEA-Y coated microextraction capillary

| Analyte class and name | Peak area reproducibility (n = 3) Mean peak area (milli absorbance unit) | RSD (%) | Detection limit (ng mL$^{-1}$) (S/N = 3) | Enrichment factors |
|---|---|---|---|---|
| Amides | | | | |
| 4-bromoacetanilide | 142.2 | 6.1 | 3.62 | 110.4 |
| N-methyl-1-naphthyl-acetamide | 61.9 | 5.3 | 5.95 | 78.9 |
| Benzanilide | 204.0 | 2.9 | 2.60 | 153.6 |
| Phenols | | | | |
| 4-flourophenol | 13.1 | 4.2 | 1.35 | 95.5 |
| 2,3-dichlorophenol | 22.8 | 4.7 | 1.19 | 135.8 |
| 2,4-dichlorophenol | 30.5 | 3.3 | 0.94 | 160.0 |
| 2,4,6-trichlorpehnol | 29.5 | 6.3 | 0.91 | 175.5 |
| 2-benzyl-4-chlorophenol | 30.1 | 2.7 | 0.96 | 155.4 |
| Pentachlorophenol | 11.0 | 6.2 | 1.28 | 116.5 |
| 4-tertoctylphenol | 7.2 | 2.8 | 1.39 | 93.0 |
| Alcohols | | | | |
| 2-naphthol | 462.6 | 1.9 | 0.83 | 300.0 |
| 1-naphthol | 198.0 | 2.9 | 1.04 | 240.0 |
| Diphenylcarbinol | 158.3 | 1.7 | 1.25 | 200.0 |
| Ketones | | | | |
| 5,5-dimethyl-1,3-cyclo-hexadione | 25.6 | 5.6 | 7.35 | 54.4 |
| 1,2-naphthoquinone | 37.8 | 3.2 | 6.85 | 58.4 |
| 1-indanone | 78.7 | 1.7 | 5.68 | 70.4 |
| 4-methoxyacetophenone | 135.3 | 3.3 | 3.85 | 104.0 |
| 4-hydroxybenzophenone | 145.0 | 4.9 | 3.65 | 109.6 |
| 2-Hydroxy-2-phenyl-acetophenone | 65.3 | 5.3 | 5.95 | 67.2 |
| Propiophenone | 159.4 | 5.2 | 3.57 | 112.0 |
| Benzophenone | 375.6 | 3.7 | 1.67 | 240.0 |
| Benzil | 361.3 | 5.3 | 1.79 | 224.0 |
| 4-chlorobenzophenone | 392.3 | 3.4 | 1.56 | 256.0 |
| Aldehydes | | | | |
| 4-Hydroxy-3-methoxy-benzaldehyde | 147.0 | 0.6 | 3.68 | 108.8 |
| 5-Nitrosalisaldehyde | 210.2 | 5.0 | 2.59 | 154.4 |
| 4-chlorobenzaldehyde | 28.1 | 5.7 | 7.35 | 60.4 |
| 5-bromobenzaldehyde | 201.4 | 6.1 | 2.78 | 144.0 |
| Polyaromatic hydrocarbons | | | | |
| Naphthalene | 61.7 | 6.8 | 0.24 | 1064.4 |
| Biphenyl | 212.2 | 5.3 | 0.18 | 1378.1 |
| Fluorene | 77.5 | 1.5 | 0.23 | 1101.3 |
| Phenanthrene | 85.8 | 3.5 | 0.22 | 1102.4 |
| Anthracene | 59.6 | 5.8 | 0.29 | 856.3 |

[a]Extraction conditions: 40 cm × 0.32 mm i.d. sol-gel BHEA-Y-coated capillary; extraction time: 20 minutes. HPLC conditions: 25 cm × 4.6 mm i.d. Eclipse XDB C-18 column (5 μm d$_p$). For amides (25 ng/mL), phenols (5 ng/mL), alcohols (10 ng/mL), ketones (25 ng/mL), and aldehydes (25 ng/mL): gradient elution from 45:55 (v/v) ACN:15 mM phosphate buffer 2.5 pH to 70% ACN from 0 to 20 minutes and 45:55 (v/v) ACN:15 mM phosphate buffer 2.5 pH from 20 to 30 minutes with a runtime of 30 minutes at 0.8 mL/min flow rate, with UV detection at 230 nm (amides, alcohols and aldehydes), 280 nm (phenols), 254 nm (ketone) For PAHs (1 ng/mL): gradient elution from 80:20 (v/v) ACN:water to 100% ACN from 0 to 20 minutes with a runtime of 20 minutes at 0.8 mL/min flow rate, with UV detection at 254 nm.

Figure 11:
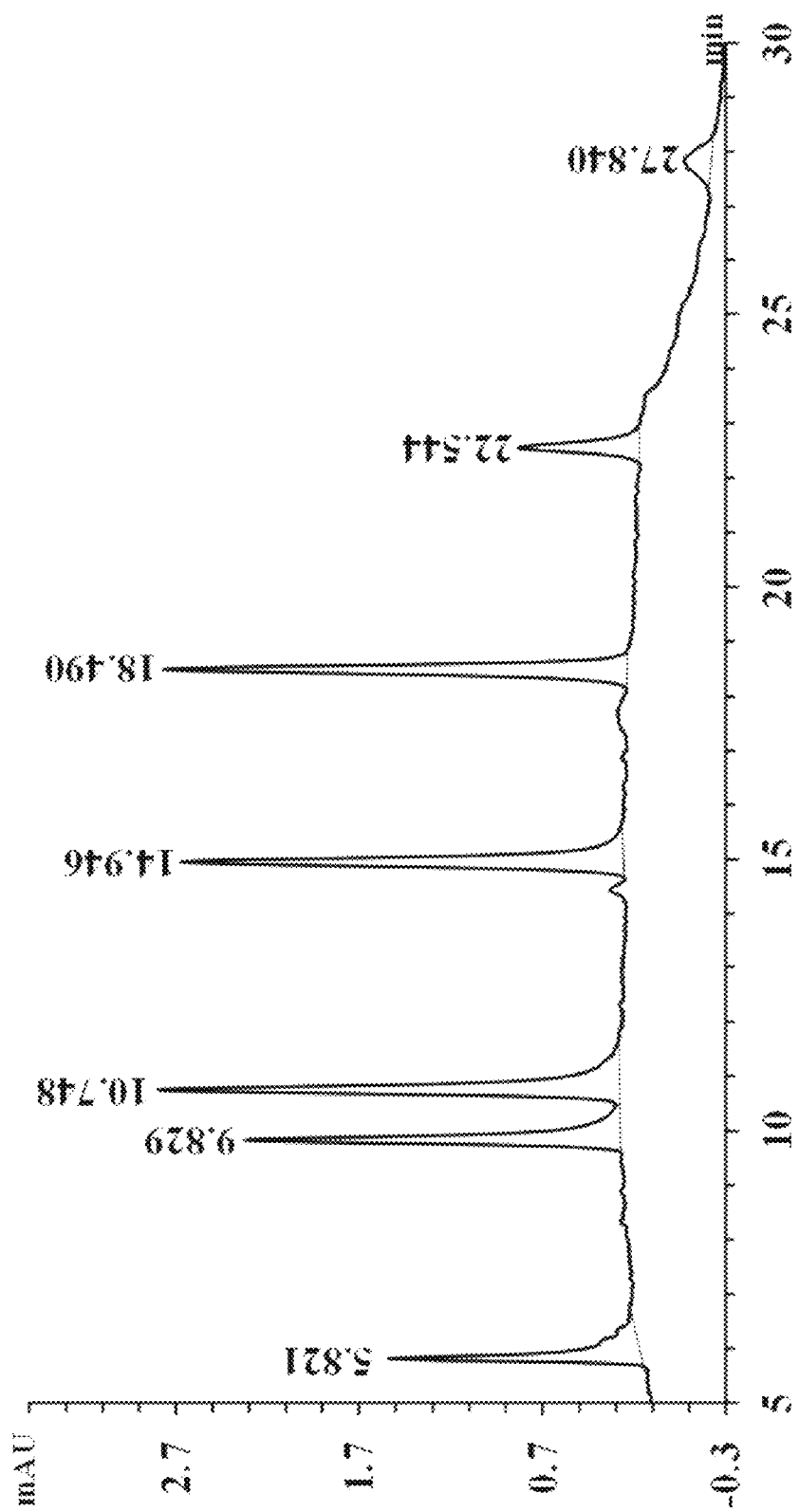
FIG. 11 shows a CME-HPLC analysis of phenols using a coated capillary within the scope of the invention.
Figure 12:
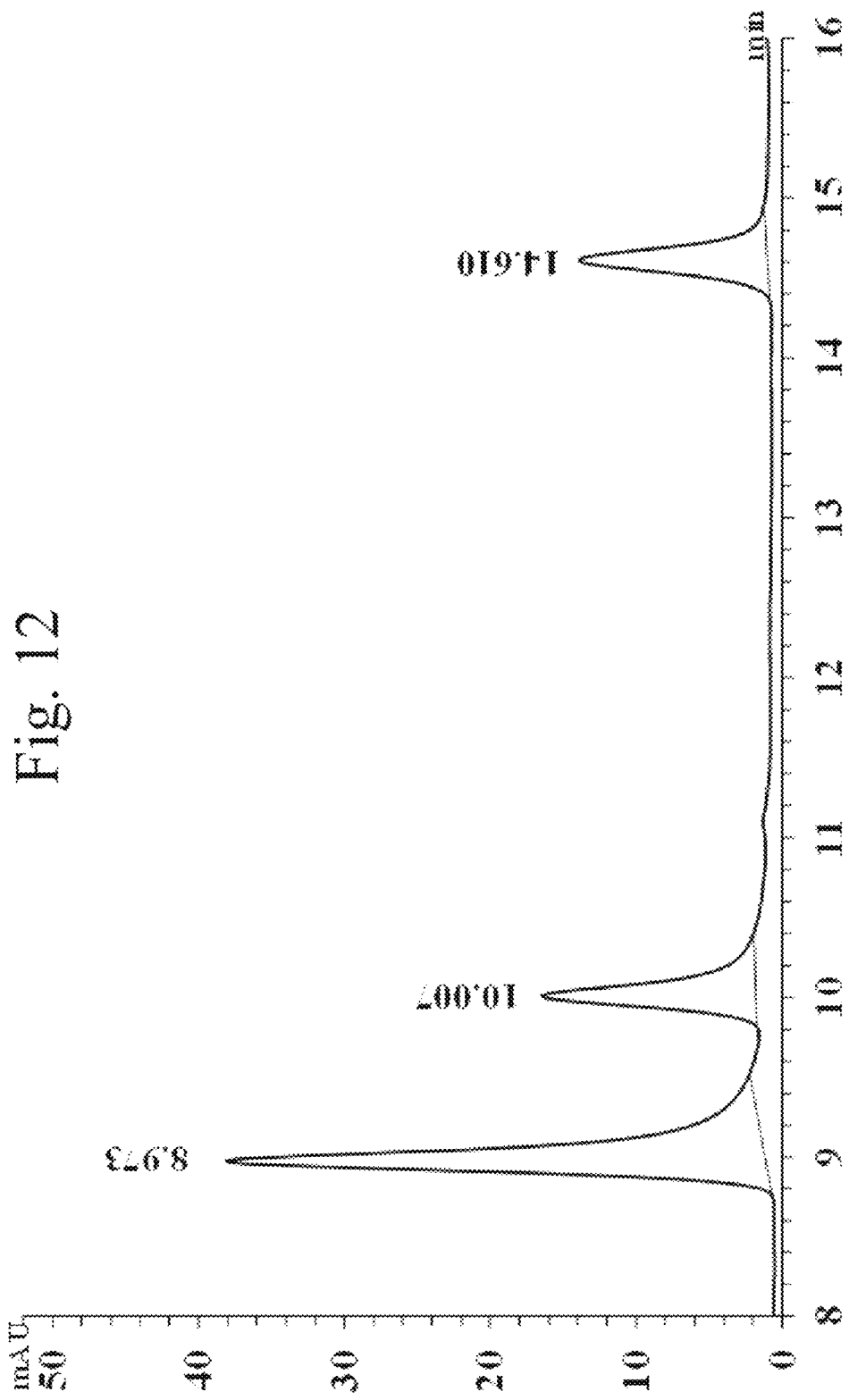
FIG. 12 shows a CME-HPLC analysis of alcohols using a coated capillary within the scope of the invention.
Figure 13:
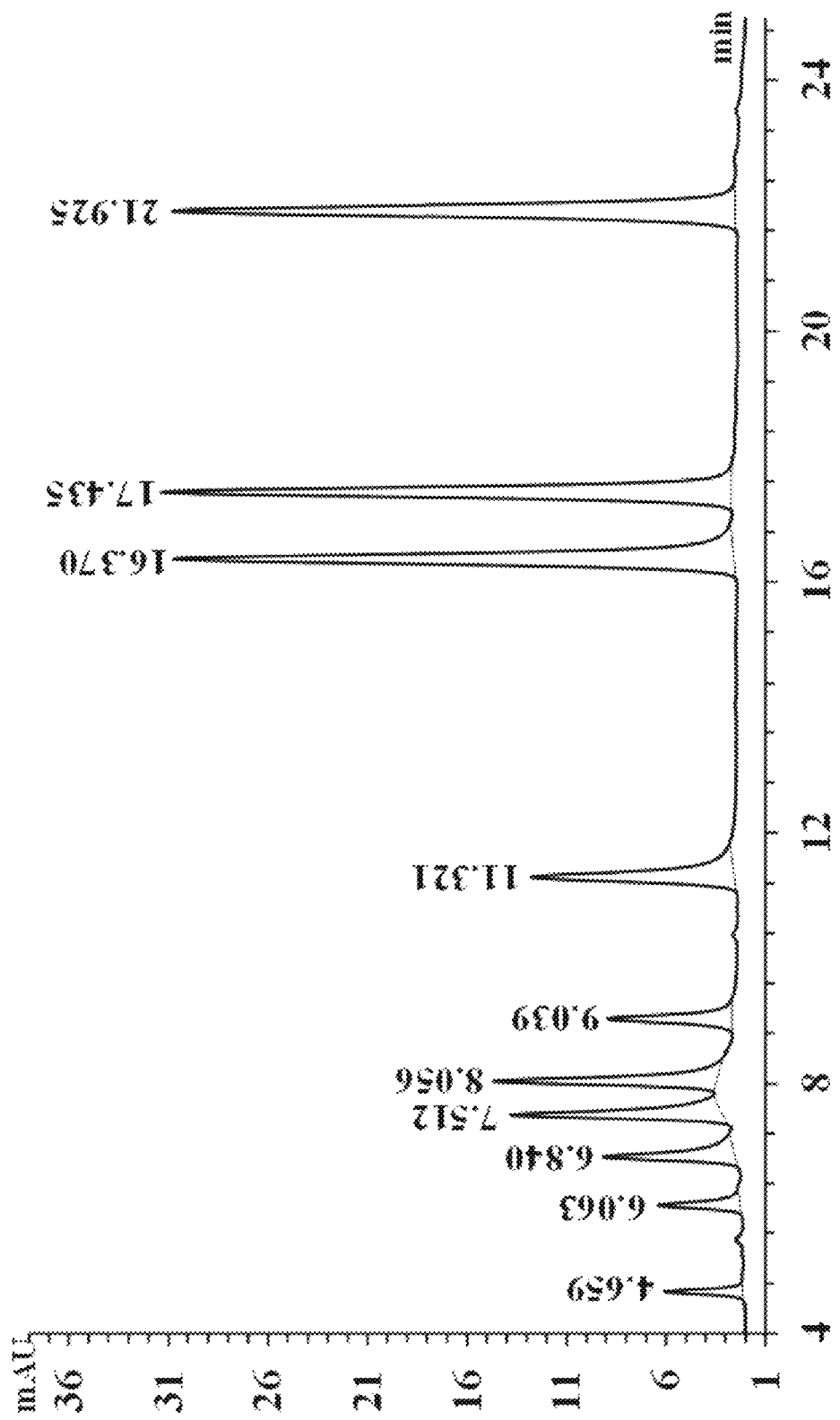
FIG. 13 shows a CME-HPLC analysis of ketones using a coated capillary within the scope of the invention.
Figure 15:
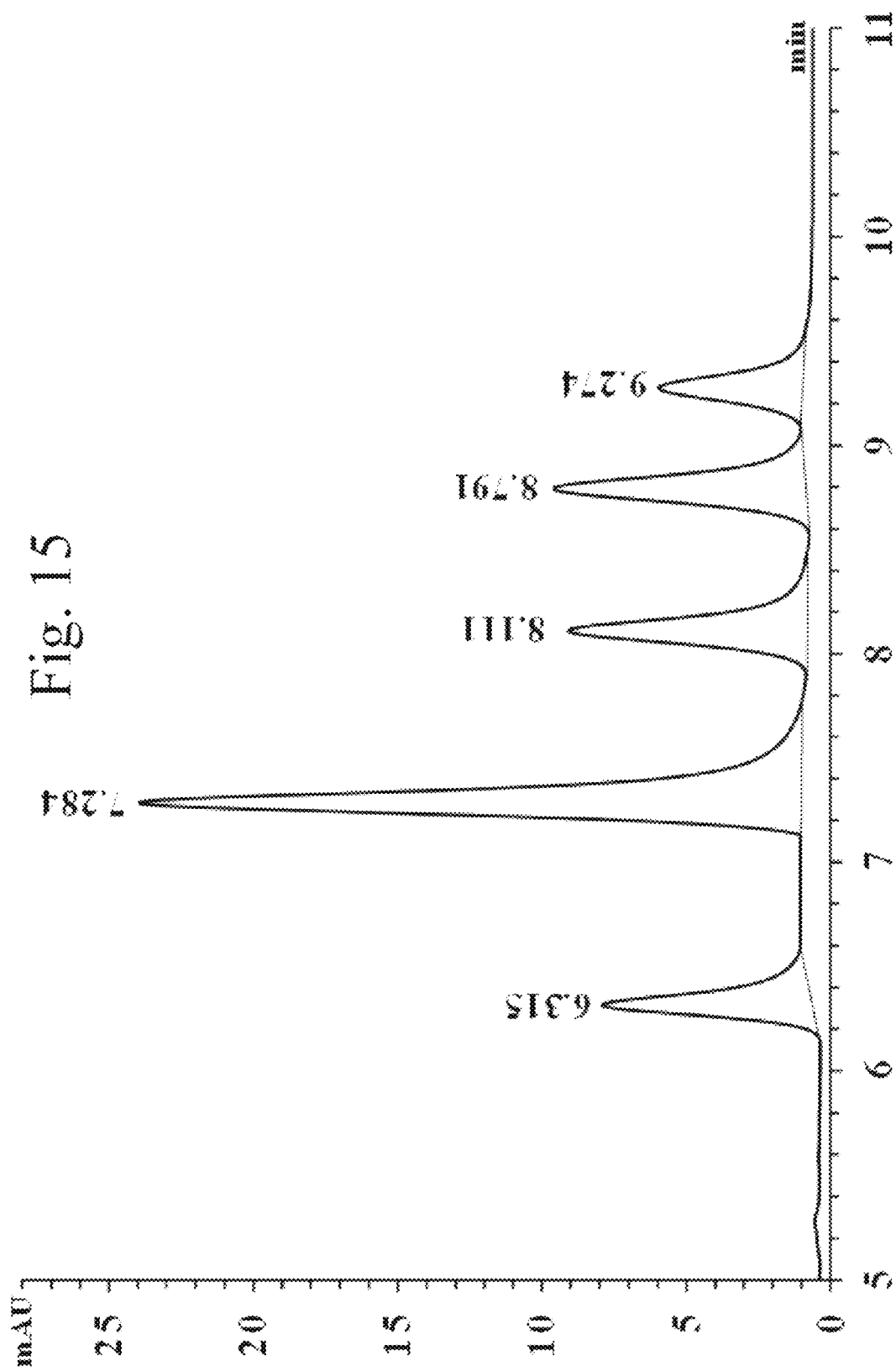
FIG. 15 shows a CME-HPLC analysis of polyaromatic hydrocarbons (PAHs) using a coated capillary within the scope of the invention.

The CME-HPLC analysis of the polar phenols using BHEA-Y coated capillary is presented in FIG. 11. The CME-HPLC analysis of the alcohols at 10 ng/mL concentration is shown in FIG. 12. FIG. 13 shows the online CME-HPLC analysis of ketones, which are considered moderately polar amongst the compounds classes. The online CME-HPLC analysis of a non-polar analyte class, i.e., polyaromatic hydrocarbons, using a BHEA-Y sol-gel coated capillary according to the invention is shown in FIG. 15.

PREPARATIVE REPRODUCIBILITY FOR BHEA-Y COATINGS: To evaluate the capillary to capillary reproducibility, a different run was designed where compounds from all the classes of varied polarities were included in the same chromatographic run. A photodiode array detector was used for this purpose, with all three desired wavelengths simultaneously irradiated. For amides, alcohols, and aldehydes, 230 nm were irradiated. Ketones and PAHs were analyzed at 254 nm. Phenols were irradiated at 280 nm. Three BHEA-Y coated capillaries of the same size (40 cm)

were cut and used for extraction. The extraction time was kept constant at 20 minutes, and a mixture of 6 compounds containing all 6 different classes was analyzed. In this analysis amides, alcohols, aldehydes, ketones, phenols, and PAHs showed 8.3, 9.9, 9.5, 4.1, 7.6 and 7.0% RSD (n=3) as shown in Table 4.

to a detailed analysis under varied parameters to validate the HPLC method. Specifically, for 7 selected phenols, a calibration curve was established, and it was found out that online CME-HPLC analysis using inventive coatings can provides a linear response of the phenols from 5 to 200

TABLE 4

Reproducibility for capillary to capillary extraction, one member from each class was selected based on well resolved peaks and retention time.

| | | | Peak area reproducibility | | | |
|---|---|---|---|---|---|---|
| Chemical class | Name | $t_P$ | Mean peak area (n = 3) Capillary 1 | Mean peak area (n = 3) Capillary 2 | Mean peak area (n = 3) Capillary 3 | Capillary to Capillary % RSD |
| Amides | 4-bromoacetanilide | 6.760 | 310.5 | 350.5 | 365.2 | 8.3 |
| Alcohols | 2-naphthol | 8.941 | 1795.2 | 1575.2 | 1918.3 | 9.9 |
| Aldehyde | 5-bromobenzaldehyde | 11.763 | 371.8 | 420.5 | 350.2 | 9.5 |
| Ketone | Benzophenone | 16.416 | 710.2 | 750.6 | 770.5 | 4.1 |
| Phenols | 2-benzyl-4-chlorophenol | 18.640 | 291.2 | 250.2 | 271.5 | 7.6 |
| PAHs | Biphenyl | 23.669 | 483.5 | 453.2 | 420.5 | 7.0 |

Figure 17A:
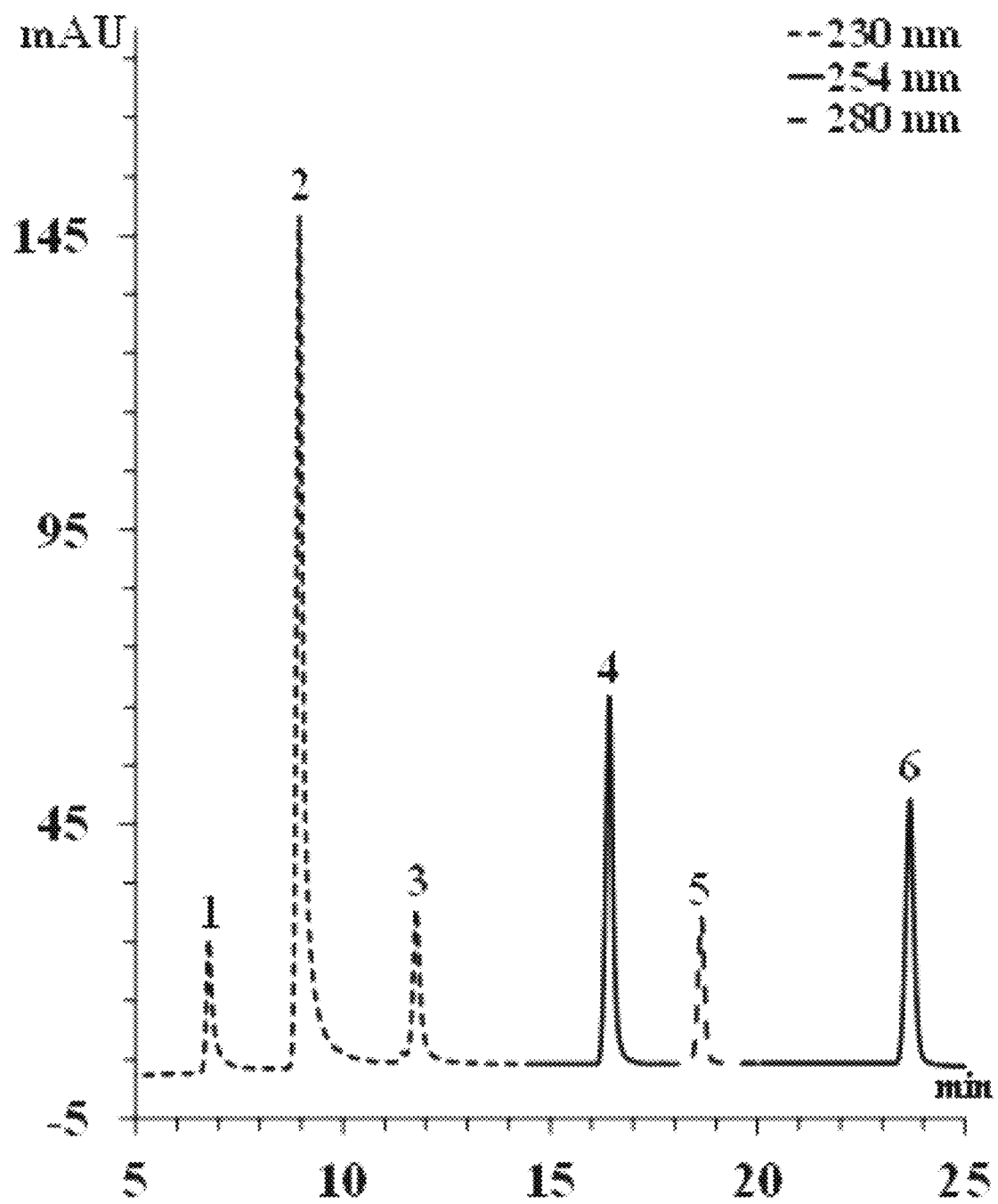
FIGS. 17A to 17C show CME-HPLC-UV comparisons for an inventive BHEA-Y sol-gel coated capillary where
Figure 17B:
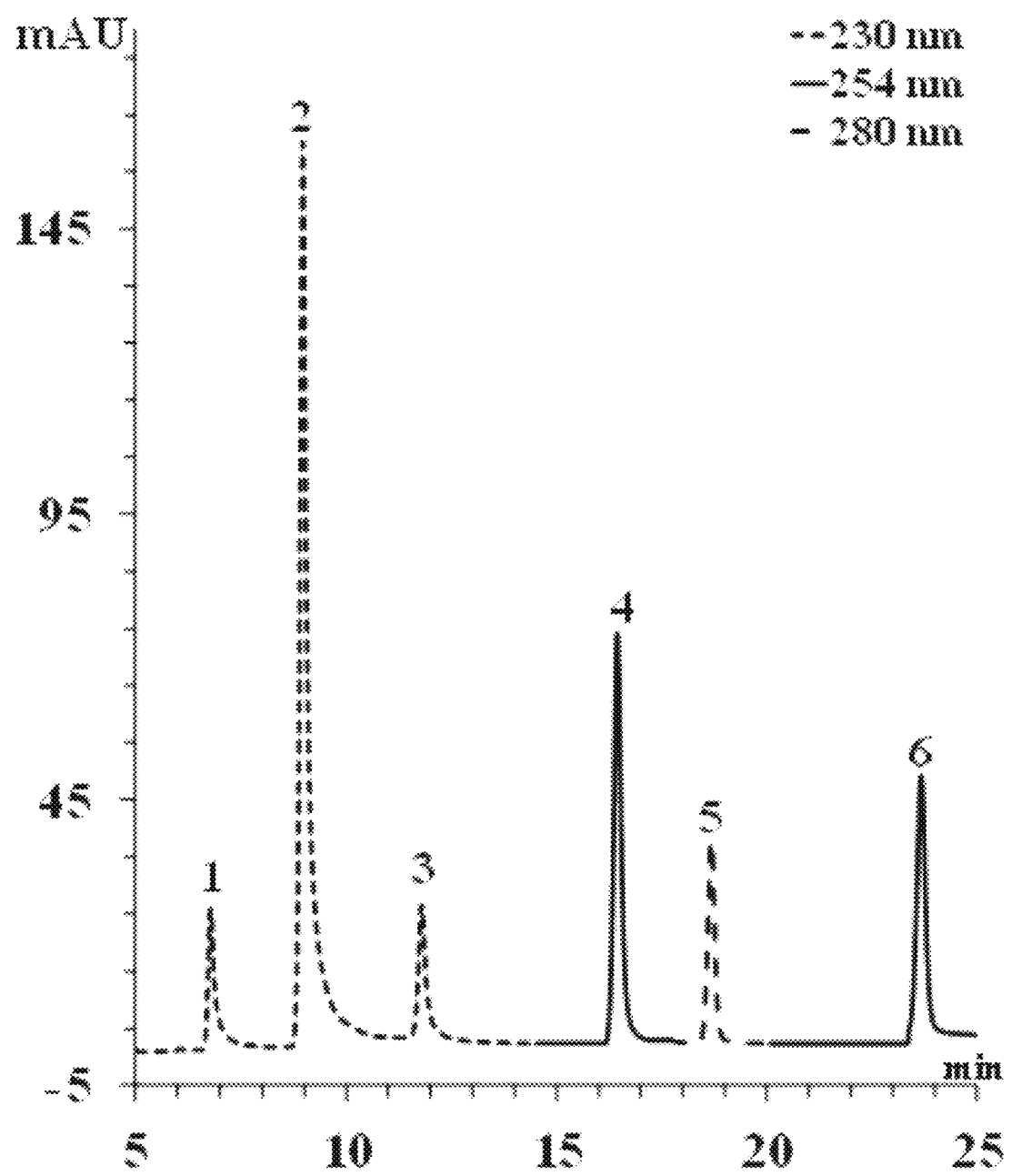
Figure 17C:
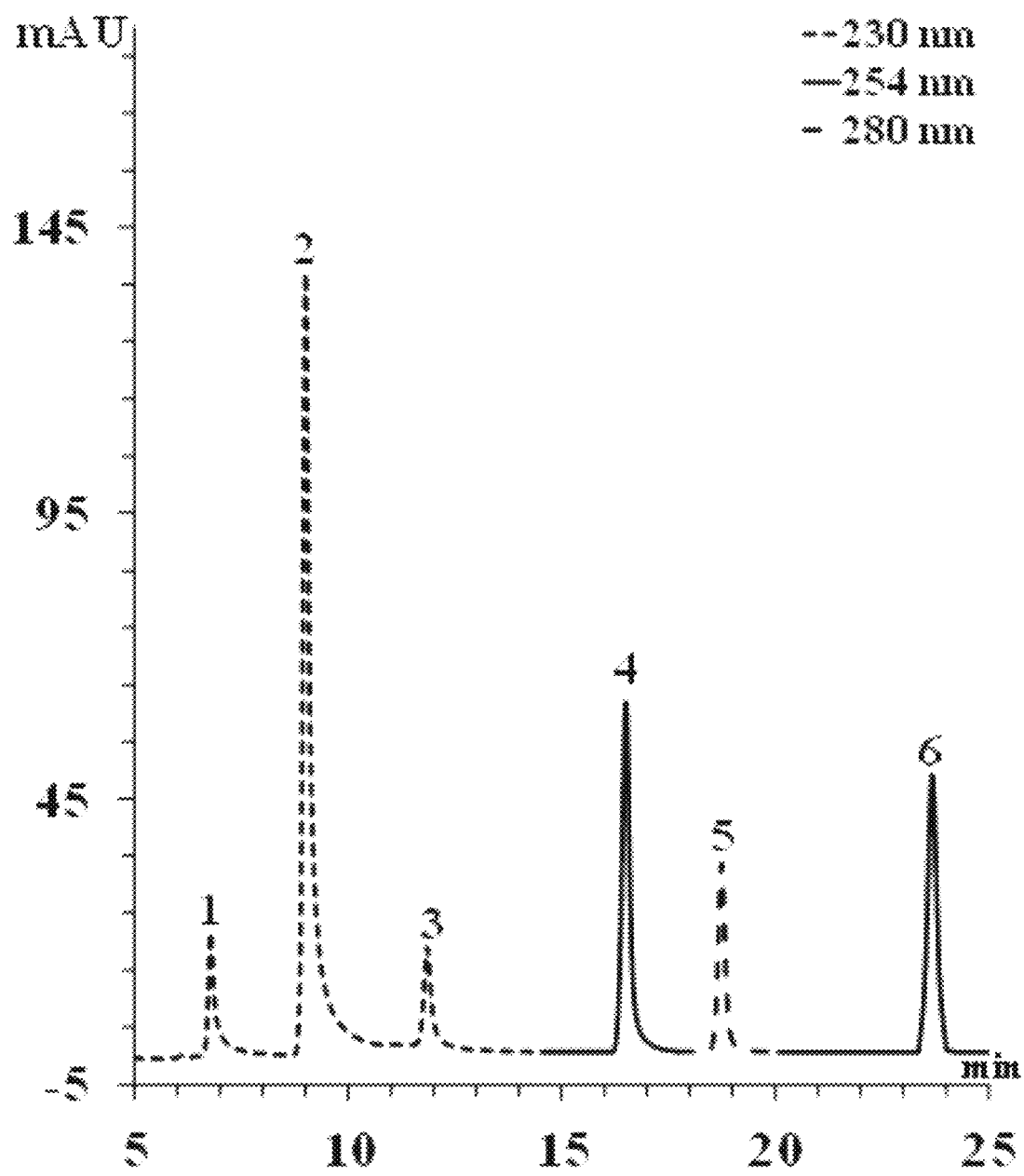

EFFECT OF EXTREME PH CONDITIONS ON EXTRACTION: The HPLC run designed for the capillary to capillary reproducibility analysis was also used for determining the stability of BHEA-Y coating. For this purpose, the coated capillaries were flushed with acidic and basic aqueous solutions for 24 hours and tested for the extraction of each analyte with different organic compound classes. FIG. 17 shows good reproducibility or ±5.0% for either condition. Although the extraction is slightly enhanced in the case of NaOH treatment, the BHEA-Y sol-gel based coating showed excellent stability in either extreme pH environment. This may be due to cleaning the inner surface and increasing the porosity of the sol-gel network.

METHOD VALIDATION PARAMETERS FOR ONLINE CME-HPLC ANALYSIS OF PHENOLS: As an established environmental pollutant, phenols were subjected ng/mL. This calibration curve was also accompanied with excellent $R^2$ values, ranging from 0.9971 to 0.9998. The higher enrichment factors, i.e., 93.0 to 175.5, allow lower detection limits, i.e., 0.91 to 1.39 ng/mL, and quantification, i.e., 3.0 to 4.6 ng/mL. The intra-day, inter-day, and capillary to capillary reproducibility were also tested to be within 10%, as shown below in Table 5. The results indicate that BHEA-Y sol-gels can provide an excellent coating material for phenol extraction with reliable accuracy and reproducibility.

TABLE 5

Analytical parameters for selected phenols.

| | | | | | | | RSD % (n = 3) | | |
|---|---|---|---|---|---|---|---|---|---|
| | | | | | | | One capillary | | |
| Analyte | Regression equation | $R^2$ | Linear range (ng mL$^{-1}$) | LOD | LOQ | Enrichment factor | Intra-day | Inter-day | C to C* |
| 4-flourophenol | y = 1.2975x + 1.2668 | 0.9992 | 5-400 | 1.35 | 4.5 | 95.5 | 4.2 | 4.8 | 5.8 |
| 2,3-dichlorophenol | y = 1.7986x + 3.9888 | 0.9998 | 5-400 | 1.19 | 3.9 | 135.8 | 4.7 | 5.0 | 6.5 |
| 2,4-dichlorophenol | y = 3.1140x + 3.7740 | 0.9988 | 5-400 | 0.94 | 3.1 | 160.0 | 3.3 | 4.2 | 7.5 |
| 2,4,6-trichloropehnol | y = 2.8494x + 1.2927 | 0.9990 | 5-400 | 0.91 | 3.0 | 175.5 | 6.3 | 6.0 | 9.2 |
| 2-benzyl-4-chlorophenol | y = 2.4693x + 4.9543 | 0.9979 | 5-400 | 0.96 | 3.2 | 155.4 | 2.7 | 3.5 | 7.6 |
| Pentachlorophenol | y = 1.3099x + 0.3402 | 0.9995 | 5-400 | 1.28 | 4.2 | 116.5 | 6.2 | 6.8 | 8.5 |
| 4-tertoctylphenol | y = 0.9870x + 0.7340 | 0.9971 | 5-400 | 1.39 | 4.6 | 93.0 | 2.8 | 4.0 | 6.8 |

*c to c capillary to capillary

Figure 18:
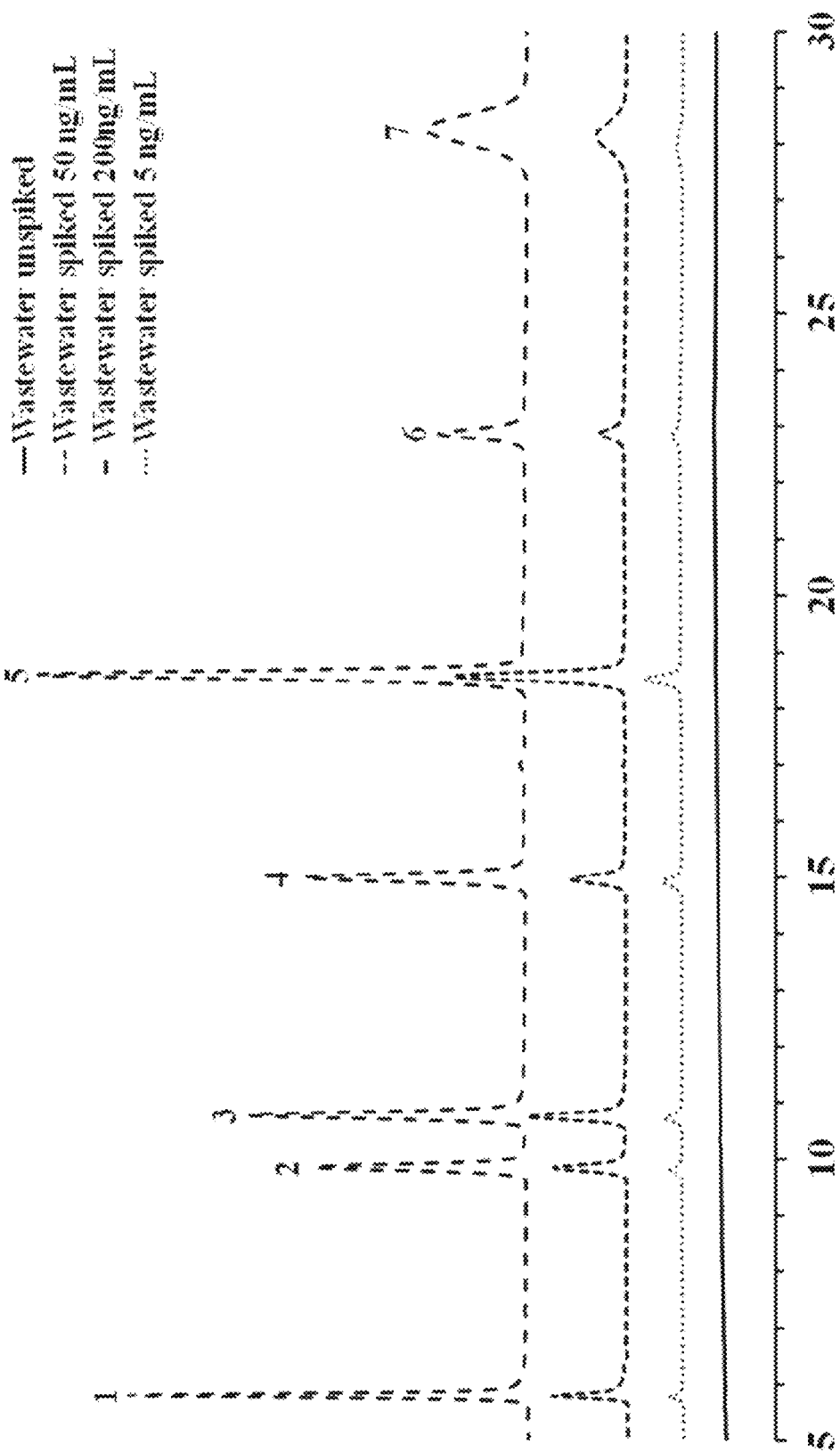
FIG. 18 shows CME-HPLC analyses of wastewater unspiked, and spiked with 5 ng/mL, 50 ng/mL, and 200 ng/mL of mixed phenols.

ONLINE CME-HPLC ANALYSIS OF PHENOLS IN REAL SAMPLES: To evaluate the applicability of the inventive CME-HPLC analysis to real samples, waste water and swimming pool water were collected and filtered using 4.5-micron filter paper. The filtered sample was passed through an inventive BHEA-Y coated capillary installed in the HPLC manual injection port for extraction and online HPLC analysis. The wastewater and pool-water samples did not show the presence of the selected phenols. However, the sample was spiked using seven phenols with concentrations of 5, 50, and 200 ng/mL, and evaluated for recovery and reproducibility. FIG. 18 shows the online CME-HPLC analysis of wastewater un-spiked and spiked with different concentrations. Table 6, below, presents the overall recoveries in wastewater, ranging between 84.7 and 92.1%, and in swimming pool-water, from 86.1 to 94.3%. The reproducibility of the results in the real samples was also excellent, within 7.6%.

TABLE 6

Analytical results of wastewater and pool water samples

| Analyte | Spiked Concentration (ng mL$^{-1}$) | Wastewater Recovery (%) | Wastewater RSD (%) | Pool-water Recovery (%) | Pool-water RSD (%) |
| --- | --- | --- | --- | --- | --- |
| 4-flourophenol | 5 | 84.7 | 4.6 | 86.2 | 5.2 |
|  | 50 | 86.9 | 6.1 | 89.0 | 5.1 |
|  | 200 | 91.1 | 3.5 | 92.2 | 3.0 |
| 2,3-dichloro-phenol | 5 | 89.0 | 3.4 | 86.1 | 3.6 |
|  | 50 | 87.5 | 4.1 | 88.6 | 3.5 |
|  | 200 | 88.7 | 6.7 | 91.1 | 4.4 |
| 2,4-dichloro-phenol | 5 | 87.8 | 2.3 | 86.2 | 2.9 |
|  | 50 | 91.8 | 6.2 | 90.9 | 5.2 |
|  | 200 | 90.6 | 5.9 | 91.9 | 5.1 |
| 2,4,6-trichloro-pehnol | 5 | 90.2 | 4.4 | 92.3 | 4.6 |
|  | 50 | 90.1 | 7.1 | 88.1 | 4.5 |
|  | 200 | 90.8 | 4.6 | 89.6 | 3.2 |
| 2-benzyl-4-chlorophenol | 5 | 89.2 | 5.7 | 90.0 | 6.2 |
|  | 50 | 91.7 | 7.6 | 90.7 | 6.9 |
|  | 200 | 90.9 | 4.1 | 91.8 | 6.5 |
| Pentachloro-phenol | 5 | 89.7 | 3.1 | 90.5 | 3.3 |
|  | 50 | 88.4 | 5.7 | 87.6 | 4.9 |
|  | 200 | 87.0 | 6.4 | 89.2 | 5.4 |
| 4-tertoctyl-phenol | 5 | 90.3 | 5.5 | 94.3 | 4.0 |
|  | 50 | 92.1 | 5.2 | 89.8 | 6.4 |
|  | 200 | 91.8 | 5.6 | 90.6 | 4.8 |

* RSD = Relative standard deviation

Further utilities of inventive sol-gels, including BHEA-Y, may be found in different classes of hazardous pollutants, or hyphenating coated capillaries with one or more analytical techniques, including gas chromatography, etc.

Inventive sol-gels, such as BHEA-Y, can be synthesized and immobilized on glass as coatings, e.g., inside capillaries, and utilized for online CME-HPLC analysis, among other things. The sol-gel technique can enable direct chemical attachment of the coatings to the inner surface of, e.g., a capillary, which may make the coatings resistant to harsh solvent and extreme pHs. BHEA-Y based coatings can have extraordinary enrichment factors for a complete range of polarities of analytes, with low detection limits and reproducible results. The method of coating can produce linear and reliable data with acceptable recovery and reproducibility in real samples, like wastewater and pool-water, e.g., for phenols and other compound classes.

Referring now to the drawings, wherein like reference numerals designate identical or corresponding parts throughout the several views.

FIG. 1 shows an exemplary online CME-HPLC analytical system, including a sample flow system (9), manual injection port (10), and an HPLC system (8). The sample flow system (9) may include at least one sample (1) and pump (2a), which may run a gradient or isocratic. The HPLC system (8) may include at least one analytical column (5), detector (6), and pump (2b), gradient or isocratic. The manual injection port (10) may include a capillary (7) in the sample injection loop, manual injection port (3), and waste outlet (4).

FIG. 2 shows a theoretical representation of the exemplary hydrolysis (top) and polycondensation of the YMEO precursor (middle), followed by anchoring of the final coating material network inside the capillary wall (bottom).

Figure 3A:
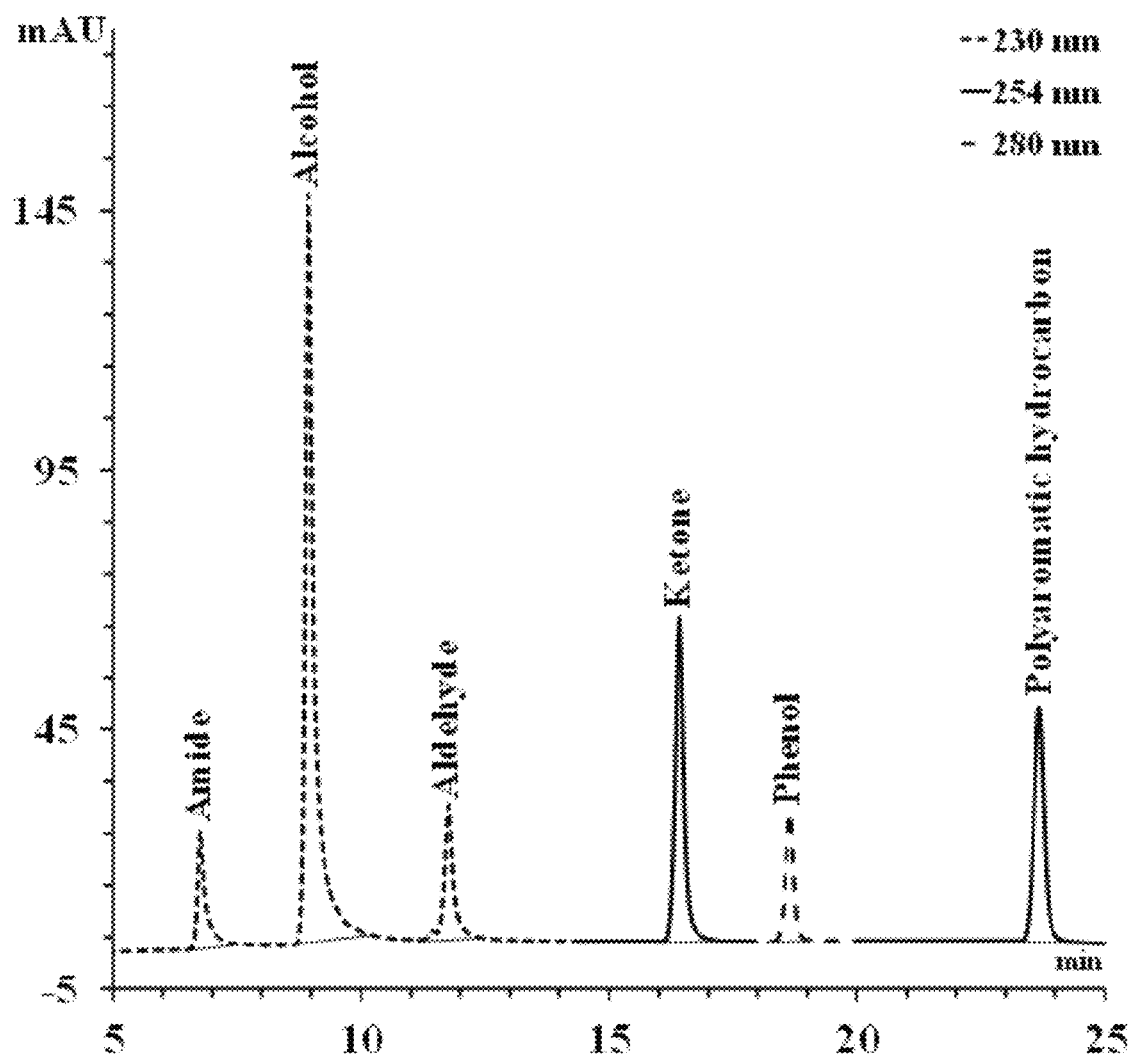
FIGS. 3A and 3B show extraction-HPLC results for representative compound classes with FIG. 3A corresponding to a capillary coated with BHEA-Y-based coating and FIG. 3B corresponding to a capillary coated with an yttria-based coating alone.
Figure 3B:
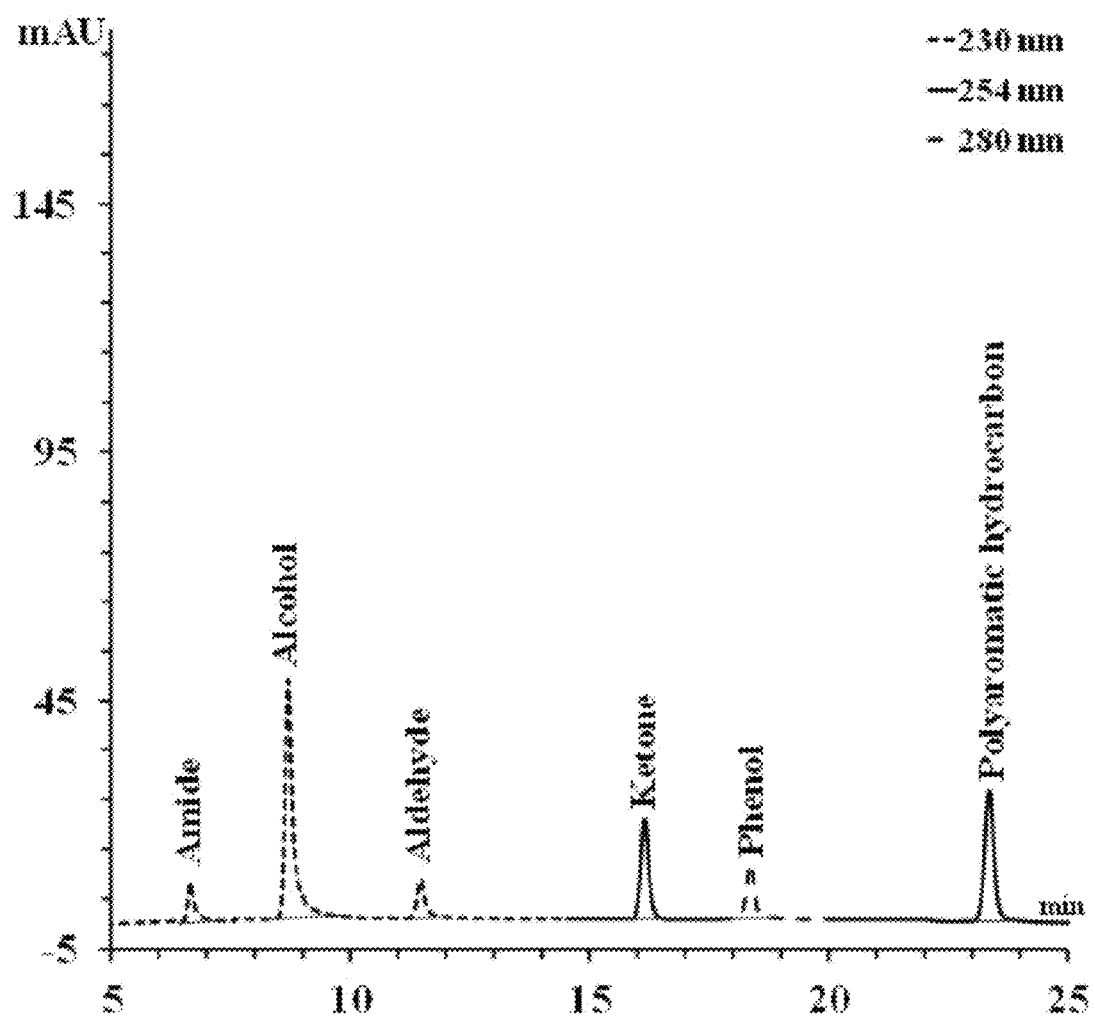

FIGS. 3A and 3B show extraction-HPLC results for representative compound classes with (A) a capillary coated with BHEA-Y-based coating (B) a capillary coated with yttria-based coating alone. The extraction conditions: 40 cm×0.32 mm i.d. capillary with an extraction time of 20 minutes. The HPLC conditions involved a 25 cm×4.6 mm i.d. Eclipse XDB C-18 column (5 μm dp) with gradient elution from 45:55 (v/v) acetonitrile (ACN): 15 mM phosphate buffer 2.5 pH to 70% ACN from 0 to 20 minutes, and 45:55 (v/v) ACN:15 mM phosphate buffer 2.5 pH from 20 to 30 minutes; runtime 30 minutes, with 0.8 mL/min flow rate, and UV detection using a photodiode array detector at 230 nm (amides, alcohols, and aldehydes), 254 nm (ketones, polyaromatic hydrocarbons), and 280 nm (phenols).

FIGS. 4A and 4B show SEM analysis of an yttrium oxide coating according to the invention inside the fused silica capillary at low (A) and high (B) magnifications, with an inset in FIG. 4B showing the thickness of hybrid polymer coated in fused-silica capillary.

FIG. 5 shows energy dispersive x-ray spectroscopy (EDS) analysis of an yttrium oxide polymer within the invention, coated inside a fused-silica capillary, and the inset table presents atomic weight (%) fractions.

Figure 7:
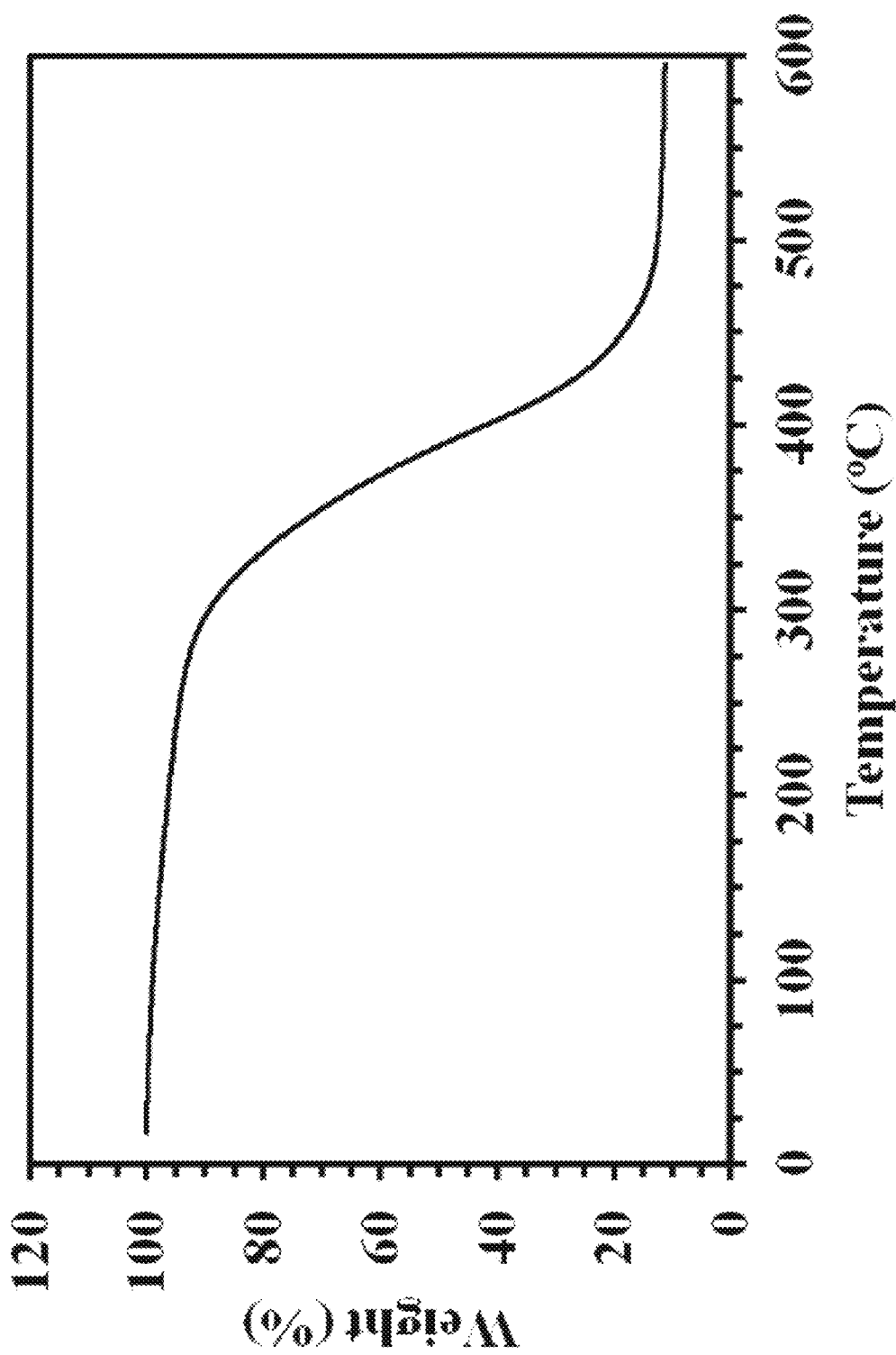
FIG. 7 shows thermogravimetric analysis (TGA) of a BHEA-Y polymer according to the invention, synthesized as described herein, before coating a fused-silica capillary.

FIG. 6A to 6E show x-ray photoelectron spectroscopy (XPS) analyses showing different bonding states of Y, C, N, O and Si of a BHEA-Y polymer synthesized as described herein before coating a fused-silica capillary FIG. 7 shows thermogravimetric analysis (TGA) of a BHEA-Y polymer according to the invention, synthesized as described herein, before coating a fused-silica capillary. The BHEA-Y sol-gel polymer was kept in an inert $N_2$ environment and the temperature was raised to 600° C. to evaluate the thermal and structural stability. A gradual loss of weight (approx. 10%) was seen from room temperature 30 to 300° C. in a first phase transition. This observation may be attributed to the loss of adsorbed water and other impurities associated with the sol-gel prepared polymer. Furthermore, gradual decomposition of the organic material network (backbone) in the polymer caused nearly 50% weight loss between 300 and 400° C. From 400 to 600° C., a phase transition indicates the complete decomposition of polymer and formation of carbon/soot. Therefore, the thermal stability and practical working temperature of the BHEA-Y polymer produced according to the Example should be in a range of from 0 to 300° C. without significant decomposition as shown in FIG. 7.

FIGS. 8A and 8B show scanning electron microscopy (SEM) images of a BHEA-Y polymer coating according to the invention, inside a fused silica capillary at low (A) and high (B) magnifications, with an in FIG. 8B showing the thickness of the coating within the fused-silica capillary. FIGS. 8A and 8B show that the BHEA-Y polymer is uniformly coated inside the fused silica of 320 μm i.d. with estimated 8.0 μm thickness. The morphology of the inner surface reveals no cracks or discontinuity of BHEA-Y coating. This may offer better accessibility and high sorption capacity of extractant during micro-extraction operation.

FIG. 9 shows an energy dispersive spectroscopy (EDS) analysis of a BHEA-Y polymer coating according to the invention, coated inside a fused-silica capillary with an inset table presenting atomic weight (%) fractions. The EDS confirms the elements present in the sol-gel coating and complements the composition analysis observed by x-ray photoelectron spectroscopy (XPS). Good correlation between the elemental weight (%) determined by EDS and the theoretical calculation from the monomers was obtained, as shown in FIG. 9 and the inset table.

FIGS. 10 to 18 show exemplary HPLC results for various analytes using the following common conditions. The extraction conditions include: (a) a 40 cm×0.32 mm i.d. BPU-BHEA sol-gel coated capillary; and (b) extraction time of 20 min. The HPLC column was a 25 cm×4.6 mm i.d. Eclipse XDB C-18 column (5 μm dp). Except for FIG. 15, gradient elution was used from 45:55 (v/v) acetonitrile (ACN): 15 mM (aq.) phosphate buffer 2.5 pH to 70% ACN from 0 to 20 minutes and 45:55 (v/v) ACN: 15 mM phosphate buffer 2.5 pH from 20 to 30 minutes, with a runtime of 30 min at 0.8 mL/min flow rate, at ambient temperature, using UV detection.

FIG. 10 shows an exemplary CME-HPLC analysis of amides using a coated capillary with the scope of the invention, using UV detection at 230 nm. HPLC peaks detected include, each at 25 ng/mL: 4-bromoacetanilide ($t_R$=6.774); n-methyl-1-naphthylacetamide ($t_R$=8.153); and benzanilide ($t_R$=10.094). Amides are considered to be polar analytes. Online CME-HPLC analysis of amides using BHEA-Y based coated capillaries gave enrichment factors (78.9 to 153.6), low detection limits ranging between 2.60 to 5.95 ng/mL (S/N=3) and reliable % RSD (less than 6.1%) where n was 3.

FIG. 11 shows an exemplary CME-HPLC analysis of phenols using a coated capillary with the scope of the invention, using UV detection at 280 nm. HPLC peaks detected include, each at 5 ng/mL: 4-fluorophenol ($t_R$=5.821); 2,3-dichlorophenol ($t_R$=9.829); 2,4-dichlorophenol ($t_R$=10.748); 2,4,6-trichlorophenol ($t_R$=14.946); 2-benzyl-4-chlorophenol ($t_R$=18.490); pentachlorophenol ($t_R$=22.544); and 4-tert-octylphenol ($t_R$=27.840). The selected phenols have higher polarity because they are halogenated. The seven selected phenols had concentrations of 5 ng/mL. The sol-gel BHEA-Y coated capillary showed extraordinary enrichment factors ranging from 93.0 to 175.5, and reproducibility less than 6.5 (n=3) with detection limits (0.91 ng/mL to 1.39 ng/mL) as shown in Table 3, above. These low detection limits and efficient extraction of polar moieties may be explained by the polarity of the yttrium oxide moiety/moieties in the BHEA-Y sol-gel coated capillary.

FIG. 12 shows an exemplary CME-HPLC analysis of alcohols using a coated capillary with the scope of the invention, using UV detection at 230 nm. HPLC peaks detected include, each at 10 ng/mL: 2-naphthol ($t_R$=8.973); 1-naphthol ($t_R$=10.007); and diphenylcarbinol ($t_R$=14.610). Alcohols are less polar than phenols but still on the higher side in polarity. It is believed that the benzene ring(s) of the selected alcohols subject the alcohols to increased interactions with the capillary coating, thereby improving performance in the online CME-HPLC analysis. The benzene rings are believed to be attracted to non-polar groups like the polydimethylsiloxane portions of the BHEA sol-gel polymer. The alcohol moiety is believed to interact with yttrium oxide moieties in the sol-gel coating. These interactions are believed to have produced higher enrichment factors (200 to 300), lower detection limits (0.83 to 1.25 ng/mL, S/N=3), and % RSD of less than 3.0 (n=3).

FIG. 13 shows an exemplary CME-HPLC analysis of ketones using a coated capillary with the scope of the invention, using UV detection at 254 nm. HPLC peaks detected include, each at 25 ng/mL: 5,5-dimethyl-1,3-cyclohexadione ($t_R$=4.659); 1,2-naphthaquinone ($t_R$=6.063); 1-indanone ($t_R$=6.840); 4-methoxyacetophenone ($t_R$=7.512); 4-hydroxybenzophenone ($t_R$=8.056); 2-hydroxy-2-phenylacetophenone ($t_R$=9.039); propiophenone ($t_R$=11.321); benzophenone ($t_R$=16.370); benzil ($t_R$=17.435); and 4-chlorobenzophenone ($t_R$=21.925). Ten representatives of general ketone class were selected for testing, including 5,5-dimethyl-1,3-cyclohexadione, 1,2-naphthoquinone, 1-indanone, 4-methoxyacetophenone, 4-hydroxybenzophenone, 2-hydroxy-2-phenylacetophenone, propiophenone, benzophenone, and benzil. The BHEA-Y sol-gel coated capillary showed excellent enrichment factors (54.4 to 256.0) for moderately polar analytes, with an excellent limit of detection range of 1.56 to 7.35 ng/mL. The reproducibility of the extraction process for ketones was within 5.6% (n=3), as seen above in Table 3.

Figure 14:
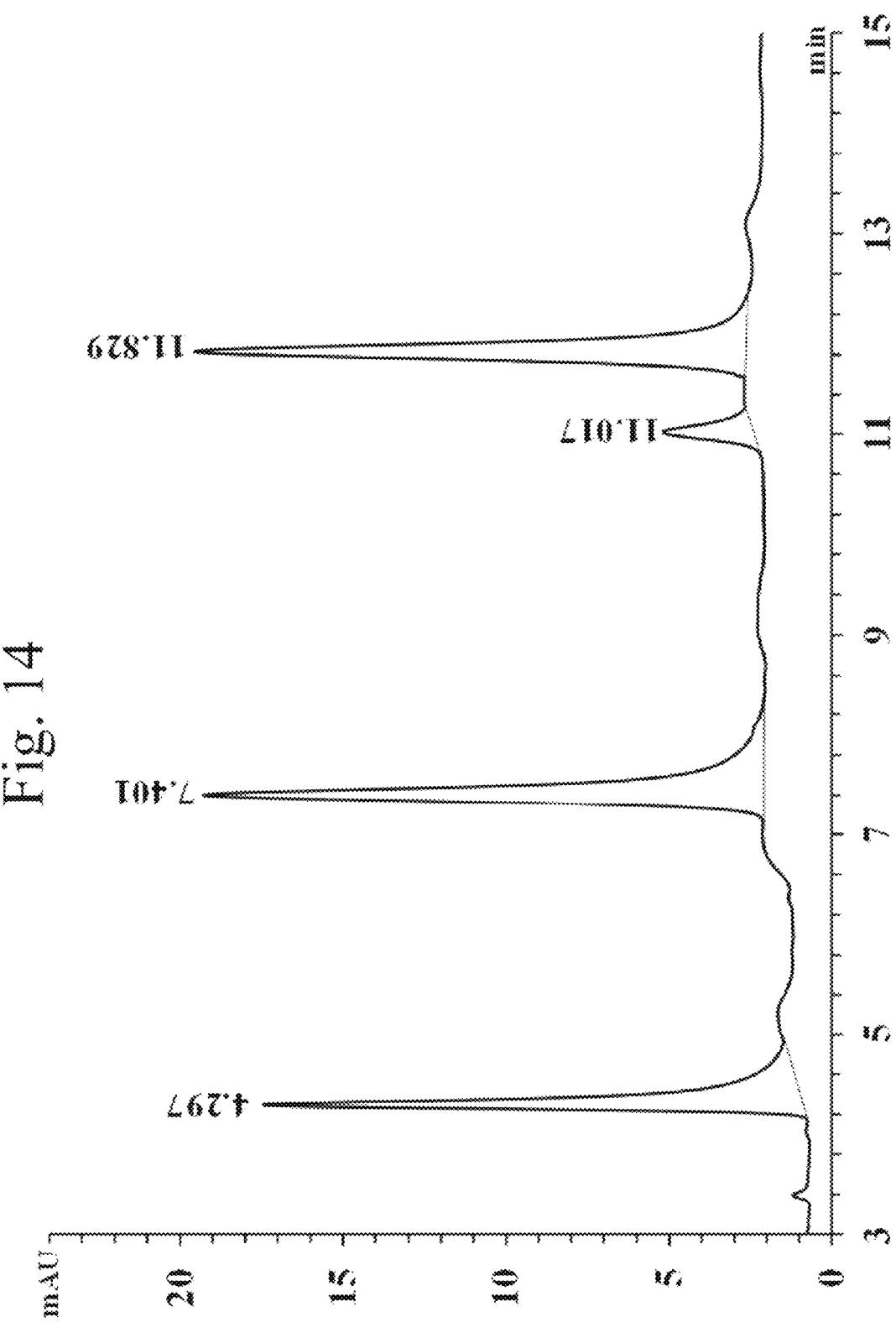
FIG. 14 shows a CME-HPLC analysis of aldehydes using a coated capillary within the scope of the invention.

FIG. 14 shows an exemplary CME-HPLC analysis of aldehydes using a coated capillary with the scope of the invention, using UV detection at 230 nm. HPLC peaks detected include, each at 25 ng/mL: 4-hydroxy-3-methoxybenzaldehyde ($t_R$=4.297); 5-nitrososalisaldehyde ($t_R$=7.401); 4-chlorobenzaldehyde ($t_R$=11.017); and 5-bromo-benzaldehyde ($t_R$=11.829). Similar extraction interactions to ketones were observed for aldehydes, as seen in FIG. 14, likely due to similar and comparable polarities of aldehydes and ketones. The CME-HPLC analysis of the four selected aldehydes at 25 ng/mL was very efficient for all the compounds, showing good reproducibility, varying less than 6.1% (n=3), low LOD, ranging between 2.59 to 7.35 ng/mL (S/N=3), and excellent enrichment factors (60.4 to 154.4).

FIG. 15 shows an exemplary CME-HPLC analysis of polyaromatic hydrocarbons (PAHs) using a coated capillary with the scope of the invention, using UV detection at 254 nm. Unlike FIGS. 10 to 14, the PAHs were eluted at 80:20 (v/v) ACN: water to 100% ACN from 0 to 20 minutes (finish), at a flow rate of 0.8 mL/min. HPLC peaks detected include, each at 1 ng/mL: naphthalene ($t_R$=6.315); biphenyl ($t_R$=7.284); fluorene ($t_R$=8.111); phenanthrene ($t_R$=8.791); and anthracene ($t_R$=9.274). For the PAH extraction procedure, five class members were selected including naphthalene, biphenyl, fluorene, phenanthrene, and anthracene. The excellent extraction performance for these compounds may be explained by the PDMS moiety in the BHEA polymer. PAH extraction gave significant enrichment factors (856.3 to 1378.1), low LODs, ranging between 0.18 to 0.29 ng/mL (S/N=3), and extraordinary % RSD, less than 6.8 (n=3).

Figure 16:
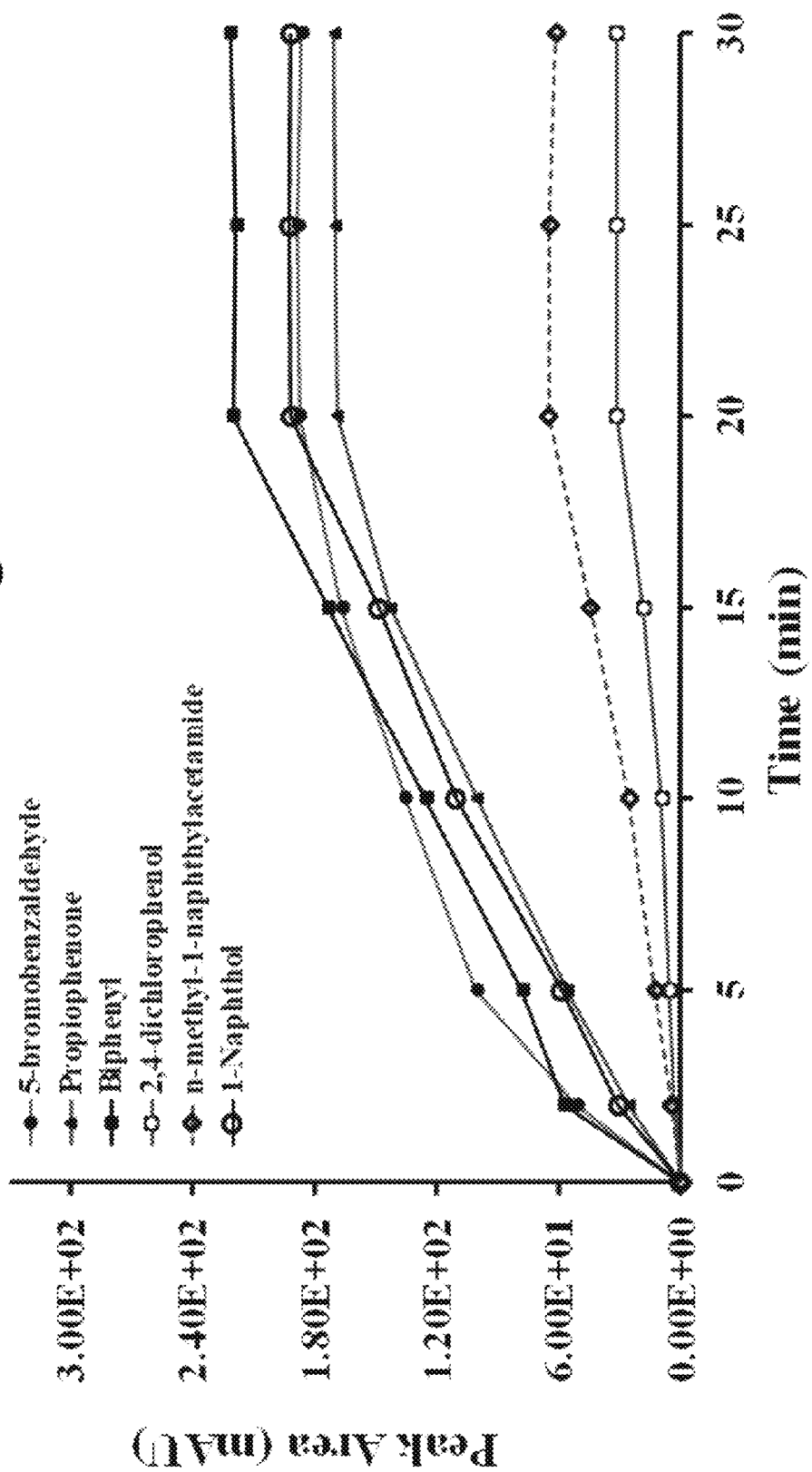
FIG. 16 shows a plot of extraction kinetics for selected analytes using a coated capillary within the scope of the invention.

FIG. 16 shows the extraction kinetic profile of the selected classes of analytes in online CME-HPLC analysis using the inventive BHEA-Y coated capillary. FIG. 16 shows a plot of extraction kinetics of a representative amide, in N-methyl-1-naphthylacetamide at 25 ng/mL, a representative phenol, in 2,4-dichlorophenol at 5 ng/mL, a representative alcohol, in 1-naphthol at 10 ng/mL, a representative ketone, in propiophenone at 25 ng/mL), a representative aldehyde, in 5-brombenzaldehyde at 25 ng/mL), and a representative PAH, in biphenyl at 1 ng/mL. One member of each compound class was selected, including n-methyl-1-naphthylacetamide (amide, polar), 2,4-dichlorophenol (phenol, polar), 1-naphthol (alcohol, polar), propiophenone (ketone, moderately polar), 5-bromobenzaldehyde (aldehyde, moderately polar), and biphenyl (polyaromatic hydrocarbon, non-polar). Several trials were conducted for the extraction of these analytes from the aqueous standard solutions. The concentrations of the analytes for the extraction kinetic profile were selected based on the quantification limit of the respective compound, at which the results are reproducible. The duration of the extraction was varied from 2 to 30 minutes, i.e., 2, 5, 10, 15, 20, 25, and 30 minutes, to evaluate the extraction kinetics. The average peak area was plotted against the extraction time. All six analytes, a representative of each compound class, showed a maximum peak area at 20 minutes, indicating that the BHEA-Y sol-gel coated capillary reaches an equilibrium after 20 minutes. The profile shows an unexpectedly superior extraction of the non-polar PAH analyte and significant extraction for moderately polar (ketones and aldehydes) and highly polar analytes (phenols).

FIG. 17 shows a CME-HPLC-UV comparison of an inventive BHEA-Y sol-gel coated capillary under three scenarios: (A) before exposing the inventive capillary to acidic or basic conditions; (B) after exposing the inventive capillary to 1.0 M NaOH for 24 hours; and (C) after exposing the inventive capillary to 1.0 M HCl for 24 hours. UV detection with a photodiode array detector was conducted at 230 nm for amides, alcohols, and aldehydes, at 254 nm for ketones and polyaromatic hydrocarbons, and at 280 nm for phenols. The following peaks, considered characteristic for the class of compounds in question were detected: peak 1=amides (4-bromoacetanilide); peak 2=alcohols (2-naphthol); peak 3=aldehydes (5-bromobenzaldehyde); peak 4=ketones (benzophenone); peak 5=phenols (2-benzyl-4-chlorophenol); and peak 6=PAHs (biphenyl).

FIG. 18 shows a CME-HPLC analysis using an inventive BHEA-Y sol-gel coated capillary of unspiked wastewater, and wastewater spiked with ng/mL, 50 ng/mL, and 200 ng/mL, on mixture of phenols. FIG. 18 illustrates the detection of peaks for the following compounds: (1) 4-fluorophenol, (2) 2,3-dichlorophenol, (3) 2,4-dichlorophenol, (4) 2,4,6-trichlorophenol, (5) 2-benzyl-4-chlorophenol, (6) pentachlorophenol, and (7) 4-tert-octylphenol.

Numerous modifications and variations of the present invention are possible in light of the above teachings. It is therefore to be understood that within the scope of the appended claims, the invention may be practiced otherwise than as specifically described herein.

REFERENCE SIGNS 1 sample
2a HPLC pump 1 (e.g., isocratic)
2b HPLC pump 2 (e.g., gradient)
3 injector
4 waste
5 analytical column with optional oven/heater
6 detector (e.g., UV-vis, ELS, $n_D$, thermal, etc.)
7 sol-gel coated capillary
8 HPLC system
9 sample flow system
10 manual injection system

The invention claimed is:
1. An analytical capillary, comprising a glass capillary and a gel coating disposed on an inner surface of the glass capillary, the gel coating having a thickness of 1 to 20 μm and comprising:
a polymer portion disposed on the inner surface of the glass capillary and a yttrium-comprising portion comprising a network comprising yttrium atoms and oxygen atoms, the yttrium-comprising portion disposed on the polymer portion,
wherein the gel coating comprises a structure (X):

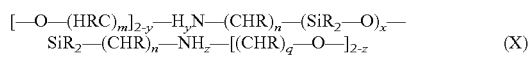
(X)

wherein R is independently H, methyl, ethyl, n-propyl, isopropyl, n-butyl, sec-butyl, isobutyl, tert-butyl, n-pentyl, tert-pentyl, isoamyl, neopentyl, C6-alkyl, phenyl, or pyridyl, y and z are independently 0 or 1, x is in a range of from 5 to 2,500, and m, n, p, and q are independently in a range of from 1 to 20.

2. The analytical capillary of claim 1, wherein R is H, x is in a range of from 25 to 500, and m, n, p, and q are independently in range of from 2 to 10.

3. The analytical capillary of claim 2, wherein x is in a range of from 30 to 250, m and q are identical, and m, n, and p are independently in range of from 2 to 4.

4. The analytical capillary of claim 3, wherein n and p are identical to each other.

5. The analytical capillary of claim 1, wherein the polymer portion is formed from [bis(hydroxyethyl)amine] (BHEA)-terminated poly dimethylsiloxane.

6. The analytical capillary of claim 1, wherein the gel coating is formed from a precursor having termini comprising hydroxyalkyl groups.

7. The analytical capillary of claim 1, wherein the glass capillary is a fused silica micro-extraction capillary.

8. The analytical capillary of claim 1, wherein the gel coating has a contact angle with water in a range of 70 to 100°.

9. A method of forming the analytical capillary of claim 1, the method comprising:
preparing a sol-gel material from a yttrium-comprising precursor and a gelling polymer; and
immobilizing the sol-gel material on the inner surface of the glass capillary to form the analytical capillary, wherein
the gelling polymer has a structure (II):

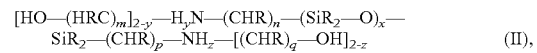
(II), wherein R is independently H, methyl, ethyl, n-propyl, isopropyl, n-butyl, sec-butyl, isobutyl, tert-butyl, n-pentyl, tert-pentyl, isoamyl, neopentyl, C6-alkyl, phenyl, or pyridyl, y and z are independently 0 or 1, x is in a range of from 5 to 2,500, and m, n, p, and q are independently in a range of from 1 to 20.

10. The method of claim 9, wherein the preparing is performed with a ratio of the gelling polymer to the yttrium-comprising precursor that is 1:2 to 1:10 by mole.

11. The method of claim 9, wherein the sol-gel material is formed in a solvent, and the solvent comprises at least 50 wt % of an alcohol based on a total weight of solvent.

12. The method of claim 9,
wherein at least 90% of the gelling polymer comprises at least one selected from the group consisting of [HO—$(H_2C)_2$]$_2$—N—$(CH_2)_2$—[Si$(CH_3)_2$—O]$_{30-50}$—Si$(CH_3)_2$—$(CH_2)_2$—N[$(CH_2)_2$OH]$_2$, [HO—$(H_2C)_3$]$_2$—N—$(CH_2)_2$[Si$(CH_3)_2$—O]$_{30-50}$—Si$(CH_3)_2$—$(CH_2)_2$—N[$(CH_2)_3$OH]$_2$, [HO—$(H_2C)_2$]$_2$—N—$(CH_2)_3$[Si$(CH_3)_2$—O]$_{30-50}$—Si$(CH_3)_2$—$(CH_2)_3$—N[$(CH_2)_2$OH]$_2$, [HO—$(H_2C)_3$]$_2$—N—$(CH_2)_3$[Si$(CH_3)_2$—O]$_{30-50}$—Si$(CH_3)_2$—$(CH_2)_3$—N[$(CH_2)_3$OH]$_2$, [HO—$(H_2C)_2$]$_2$—N—$(CH_2)_4$[Si$(CH_3)_2$—O]$_{30-50}$—Si$(CH_3)_2$—$(CH_2)_4$—N[$(CH_2)_2$OH]$_2$, [HO—$(H_2C)_4$]$_2$—N—$(CH_2)_2$[Si$(CH_3)_2$—O]$_{30-50}$—Si$(CH_3)_2$—$(CH_2)_2$—N[$(CH_2)_4$OH]$_2$, [HO—$(H_2C)_3$]$_2$—N—$(CH_2)_4$[Si$(CH_3)_2$—O]$_{30-50}$—Si$(CH_3)_2$—$(CH_2)_4$—N[$(CH_2)_3$OH]$_2$, [HO—$(H_2C)_4$]$_2$—N—$(CH_2)_3$[Si$(CH_3)_2$—O]$_{30-50}$—Si$(CH_3)_2$—$(CH_2)_3$—

$N[(CH_2)_4OH]_2$, and $[HO-(H_2C)_4]_2-N-(CH_2)_4[Si(CH_3)_2-O]_{30-50}-Si(CH_3)_2-(CH_2)_4-N[(CH_2)_4OH]_2$.

13. The method of claim 9, wherein the gelling polymer is [bis(hydroxyethyl)amine] (BHEA)-terminated polydimethylsiloxane.

14. The method of claim 9, comprising:
hydrolyzing the yttrium-comprising precursor to produce an intermediate comprising a Y-OH moiety; and
polycondensing the intermediate to form a network comprising yttrium atoms and oxygen atoms,
wherein the yttrium-comprising precursor has a structure (I)

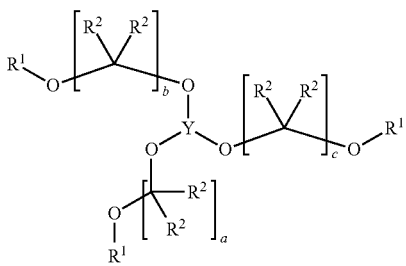

wherein $R^1$ is independently H, methyl, ethyl, n-propyl, isopropyl, n-butyl, sec-butyl, isobutyl, tert-butyl, n-pentyl, tert-pentyl, isoamyl, neopentyl, or C6-alkyl, $R^2$ is independently H, methyl, ethyl, propyl, or F, and a, b, and c are independently in a range of from 1 to 20.

15. The method of claim 14, wherein, in the yttrium-comprising precursor, $R^1$ is H, methyl, ethyl, or propyl, $R^2$ is H, and a, b, and c are in range of from 2 to 10.

16. The method of claim 14, wherein at least 90% of the yttrium-comprising precursor comprises at least one selected from the group consisting of tris(methoxymethoxy) yttrium, tris(methoxyethoxy) yttrium, tris(ethoxyethoxy) yttrium, tris(methoxypropoxy) yttrium, tris(ethoxypropoxy) yttrium, tris(propoxypropoxy) yttrium, tris(methoxybutoxy) yttrium, tris(ethoxybutoxy) yttrium, tris(propoxybutoxy) yttrium, tris(butoxybutoxy) yttrium, tris(methoxypentanoxy) yttrium, tris(ethoxypentanoxy) yttrium, tris(propoxypentanoxy) yttrium, and tris(butoxypentanoxy) yttrium.

17. The method of claim 14, wherein the yttrium-comprising precursor is yttrium methoxyethoxide (YMEO).

18. A micro extraction method, comprising
passing a dissolved sample into the analytical capillary of claim 1; and optionally
passing an eluant comprising acetonitrile and/or water through the analytical capillary.

19. An analytical method for analyzing the content of a diluted sample, comprising
passing the diluted sample into the analytical capillary of claim 1;
passing an eluant through the analytical capillary;
desorbing an extracted analyte from the analytical capillary to pass the extracted analyte onto an analytical column; and
eluting the analytical column.

20. A method of enhancing analytical sensitivity, the method comprising:
combining the analytical capillary of claim 1 in series with a high performance liquid chromatography (HPLC) column or gas chromatography (GC) column.

* * * * *